United States Patent [19]

Marangos

[11] Patent Number: 5,677,288
[45] Date of Patent: Oct. 14, 1997

[54] USE OF AMINOGLYCOSIDES TO PROTECT AGAINST EXCITOTOXIC NEURON DAMAGE

[75] Inventor: Paul J. Marangos, Encinitas, Calif.

[73] Assignee: Cypros Pharmaceutical Corporation, Carlsbad, Calif.

[21] Appl. No.: 228,229

[22] Filed: Apr. 15, 1994

Related U.S. Application Data

[63] Continuation-in-part of Ser. No. 855,600, Mar. 20, 1992, abandoned, which is a continuation-in-part of Ser. No. 700,765, May 15, 1991, abandoned.

[51] Int. Cl.$^6$ .................................................. A61K 31/70
[52] U.S. Cl. ............................... 514/39; 514/35; 514/36; 514/37; 514/38; 514/40
[58] Field of Search ............................... 514/30, 36, 37, 514/38, 39, 40, 35

[56] References Cited

U.S. PATENT DOCUMENTS

| | | | |
|---|---|---|---|
| 4,446,155 | 5/1984 | Osterholm | 424/350 |
| 4,985,458 | 1/1991 | Nakayama | 514/533 |
| 5,037,846 | 8/1991 | Saccomane et al. | 514/419 |
| 5,122,596 | 6/1992 | Phillips et al. | 530/350 |
| 5,227,397 | 7/1993 | Saccomano et al. | 514/419 |
| 5,256,684 | 10/1993 | Marshall | 514/39 |

OTHER PUBLICATIONS

Chemical Abstracts 115: 41827m (Mikami, 1991).
Caputy, A.J., et al. "The neuromuscular blocking effect of various antibiotics on normal rat skeletal muscle: A quantitative comparison," *J. Pharmacol. Exp. Ther. 217:* 369–378 (1981).
Wright, J.M., and Collier, B., "The effects of neomycin upon transmitter release and action," *J. Pharmacol. Exp. Ther. 200:* 567–587 (1977).
Knaus, H.G., et al. "Neurotoxic aminoglycoside antibiotics are potent inhibitors of 125–I Omega–Conotoxin GVIA binding to guinea pig cerebral cortex membranes," *Naunyn Schmiederberg's Arch. Pharmacol.* 336: 583–586 (1987).
Kasai, H., et al. "Presynaptic Ca–antagonist omega–conotoxin irreversibly blocks N–type ca–channels in chick sensory neurons," *Neurosci. Res. 4:* 228–235 (1987).
*Physician's Desk Reference* (1990 edition, p. 1981).
Morel, N. et al. "Factors affecting activity of cerebral microvessels and their sensitivity to calcium antagonists," pp. 283–295 in Krieglstein, J., and Oberpichler, H., *Pharmacology of Cerebral Ischemia* (Wissenschaftliche Verlagsgesellschaft mbH, Stuttgart, 1990).
Whittingham, S., et al., "In vitro model of ischemia: metabolic and electrical alterations in the hippocampal slice," *J. Neuroscience 4:* 793–802 (1984).
Schurr, A. and Rigor, B.M., "Modeling neurodegeneration and neuroprotection in hippocampal slices," pp. 24–43 in *Emerging Strategies in Neuroprotection* (Marangos and Lal, eds., Birkhauser Publ., Boston, 1992).
Keith, R.A., et al. "Actions of Neomycin on Neuronal L–, N–, and Non–L/Non–N–Type Voltage Sensitive Calcium Channel Blockers," *Journal of Molecular Neuroscience 3:* 147–154 (1992).
Perrier, M.L., et al. "Dihydropyridine–[resistant] and omega–Conotoxin–Resistant, Neomycin–Sensitive Calcium Channels Mediate the Depolarization–Induced Increase in Internal Calcium Levels in Cortical Slices from Immature Rat Brain," *Journal of Pharmacology and Experimental Therapeutics 261:* 324–330 (1992).
Yamada, K., et al. "Neuropharmacological Characterization of Voltage–Sensitive Calcium Channels: Possible Existence of Neomycin–Sensitive, Conotoxin GVIA– and Dihydropyridines–Resistant Calcium Channels in the Rat Brain," *Japanese Journal of Pharmacology 63:* 423–432 (1993).

*Primary Examiner*—Elli Peselev
*Attorney, Agent, or Firm*—Patrick D. Kelly

[57] ABSTRACT

A method is disclosed for reducing excitotoxic damage to neurons, which can occur as a result of stroke, cardiac arrest, or other events or conditions. This method involves administering an aminoglycoside that suppresses the flow of calcium ions into neurons through N-type calcium channels. To be effective for such use, an aminoglycoside must suppress N-channel activity at a potency greater than streptomycin. Aminoglycosides which meet this criterion (which includes neomycin and Gentamicin) can suppress the depolarizing activation of neurons, which in turn controls the release of glutamate, a neurotransmitter that becomes an endogenous toxin under excitotoxic conditions. Numerous aminoglycosides were tested in in vitro screening tests using brain cell membrane fragments to evaluate N-channel blocking potency. Aminoglycosides with the highest N-channel blocking potency were then tested using (1) in vitro tests on hippocampal brain tissue, to evaluate recovery of neuronal activity after a period of oxygen deprivation; (2) in vivo tests to evaluate the control of induced seizures in intact adult mammals; and (3) in vivo tests to evaluate the reduction of brain damage due to surgically-induced ischemia in intact adult mammals. The results showed that (1) aminoglycosides which are more potent than streptomycin in blocking N-channel ion flow are effective in reducing excitotoxic brain damage, without causing undesired side effects, and (2) the effectiveness of all BBB-permeable aminoglycosides tested to date in preventing excitotoxic brain damage is directly correlated with their potency in suppressing N-channel activity. Evaluation of chemical structures also indicates a correlation between the number of primary amino groups on an aminoglycoside, and its potency as an N-channel blocker and neuroprotective agent.

15 Claims, 8 Drawing Sheets

USE OF AMINOGLYCOSIDES TO PROTECT AGAINST EXCITOTOXIC NEURON DAMAGE

RELATED APPLICATION

This application is a continuation-in-part of U.S. patent application Ser. No. 07/855,600, filed on Mar. 20, 1992, now abandoned which was a continuation-in-part of patent application Ser. No. 07/700,765, filed on May 15, 1991, now abandoned.

BACKGROUND OF THE INVENTION

This invention relates to pharmacology and neurology, and involves drugs that can prevent or reduce nerve cell death or damage due to conditions such as stroke, drowning, cardiac arrest, or various injuries or diseases.

Neurons and entire regions of the brain can be severely damaged or killed during conditions or events such as strokes, drowning, carbon monoxide poisoning, cardiac arrest, or internal hemorrhaging due to rupture of an aneurysm. Various types of head injuries or other physical traumas, surgical damage, and certain types of poisons can also lead to permanent brain damage involving "excitotoxicity" (discussed below), which involves the excessive release or abnormal accumulation of excitatory neurotransmitters such as glutamic and aspartic acid. Seizures or convulsions due to epilepsy, head trauma, or other causes also involve the excessive release of excitatory neurotransmitters; although relatively mild seizures are not presumed to cause neuronal death or permanent damage, some types of severe seizures which cannot be halted by normal drugs, such as temporal lobe epilepsy (status epilepticus), are believed to cause permanent brain damage and neuronal death due to excitotoxicity. In addition, several types of progressive neurodegenerative diseases such as Alzheimer's disease, Parkinson's disease and amyotrophic lateral sclerosis (ALS) are also believed to involve excessive neurotransmitter release or accumulation as a component of the disease process.

These problems are severely aggravated by the inability of nerve cells to regenerate or repair themselves after injury; a child who suffers only a few minutes of perinatal asphyxia during birth may spend an entire lifetime horribly crippled by the injuries such damage can inflict, and many people who have suffered from strokes live the remainder of their lives partially paralyzed or unable to speak or remember major events in their lives. Brain damage is an extremely pressing medical problem which inflicts devastating suffering and tragedy on individuals and their families, and enormous expense on insurance companies and government agencies. These costs are so high, largely because pharmaceutical management of neuron damage is woefully inadequate. Although stroke is the third leading cause of death in the United States, there is, at present, not a single drug treatment which has been approved by the Food and Drug Administration for preventing or reducing brain damage due to stroke.

General Background on Neurons

During the past ten years, neurological studies have greatly increased our understanding of what happens to neurons when they are injured. What follows is a very brief overview intended to establish some basic terminology and direct the reader's attention to several structures and processes that are involved in the subject invention. Obviously, an overview cannot adequately depict the massive complexity of the mammalian brain; tens of thousands of scientific and medical articles have been published which describe various aspects of neurons and the central and peripheral nervous systems, and multi-volume treatises such as Adelman's *Encyclopedia of Neuroscience* have also been published. However, despite all that is known about neurons and neurochemistry, some simple facts (such as the complete absence of any approved treatments to reduce brain damage due to stroke, the widespread occurrence of mental illness in society, and the inability of scientists to cure or even understand the causes of most neurodegenerative diseases) clearly show that what is not known about the brain is at least as large and important as what is known.

A neuron in the central nervous system (CNS) consists of a cell body and a strand-like projection called an axon, which branches out into hundreds or even thousands of smaller fibrils called synaptic processes. Each fibril terminates at a synaptic terminus, containing a small bulb-shaped area (a bouton) which is bathed in extra-cellular synaptic fluid. The fluid fills a gap between the synaptic terminus and a receptor surface on an adjacent neuron.

Stored at the end of each synaptic process are neurotransmitter molecules. The most important excitatory neurotransmitter in the mammalian CNS is glutamate, the ionized form of glutamic acid, an amino acid. When a nerve impulse reaches the end of a glutamate-containing axon, the glutamate molecules stored in the end of the axon are released into the extracellular synaptic fluid. These molecules temporarily bind to and react with glutamate receptors on the surface of the adjacent neuron, thereby triggering a cellular reaction which causes the opening of an ion channel.

In a healthy resting state, a neuron in the CNS maintains gradients of certain ions; calcium and sodium ions ($Ca^{++}$ and $Na^+$) are maintained at low concentrations inside neurons, while potassium ions ($K^+$) are maintained at high concentrations. This is done by various ion pumping mechanisms, and by proteins which chelate free ions (i.e., which bind them in larger molecules, thereby removing the ionic form from the intracellular liquid) if the ionic concentration exceeds a certain level. The $Ca^{++}$ gradient is quite steep; the typical concentration outside a neuron is roughly $10^4$ orders of magnitude higher than inside a resting neuron.

When an ion channel is opened, certain types of ions can flow through the channel and cross the cell membrane, thereby passing from the region of high concentration to the region of low concentration. For example, when an NMDA receptor (discussed below) is triggered by a molecule of glutamate, the NMDA ion channel opens and allows $Ca^{++}$ and $Na^+$ to flow into the cell and $K^+$ to flow out. The flow of ions through such a channel is usually referred to as membrane depolarization, since it reduces the ion gradients across the membrane.

The "excitatory amino acid" (EAA) system uses two amino acids, glutamate and aspartate, as neurotransmitter molecules; either type of molecule (glutamate or aspartate) can activate any EAA receptor. Although these amino acids are two of the "common" or "primary" amino acids used to make all protein, they cannot permeate through the blood-brain barrier (BBB), and their concentration is carefully regulated inside the brain. Since glutamate is used much more frequently than aspartate as a neurotransmitter, EAA receptors are sometimes referred to as glutamate receptors.

There are at least three major classes of EAA receptors which are linked to ion channels. These are generically classified as ionotropic receptors, to distinguish them from an entirely different family of receptors called metabotropic receptors. The most widespread type of ionotropic EAA receptor can be selectively activated (in tissue culture) by an aspartate derivative called N-methyl-D-aspartate (NMDA); therefore, these receptors are called NMDA receptors, even though NMDA does not normally exist in the brain and cannot penetrate the BBB (it is used only for laboratory studies). A second class of ionotropic EAA receptors are called kainic acid (KA) receptors. The third known class of ionotropic EAA receptors are known by two different names, QUIS and AMPA, which can be confusing. Quisqualate (QUIS) was the first drug which was discovered to preferentially activate these receptors, so most articles prior to about 1988 refer to them as QUIS receptors. However, QUIS has a substantial amount of cross-reactivity with a metabotropic EAA receptor, and a different drug known as AMPA (amino hydroxymethyl isoxazole propionic acid) was later discovered to activate QUIS ionotropic receptors very selectively, with little affinity for the EAA metabotropic receptor; therefore, most current research on QUIS/AMPA ionotropic receptors uses AMPA, and the trend is toward identifying these receptors as AMPA receptors.

KA and AMPA ionotropic receptors are often grouped together and referred to as "non-NMDA receptors," since they share certain electrophysiological properties.

Excitotoxicity

Under normal and healthy conditions, glutamate molecules that are released into a synapse during a nerve impulse transmission are transported back into a neuron within a few milliseconds after the molecules have reacted with EAA receptors. This process of very rapid glutamate uptake back into the neurons is highly important, since it prevents glutamate from accumulating in the synapses and continuously activating the receptor.

However, the glutamate uptake system, like many other neuronal functions, requires energy to drive the molecular processes involved. That energy is derived from oxygen and glucose, which must be continuously delivered to the brain by the blood because the brain does not store or maintain a reserve supply of these energy resources. Neurons consume large amounts of energy (roughly one-fifth of the oxygen and glucose consumed by the entire body is consumed in the brain), and they are totally dependent on the blood for their energy needs. Therefore, it is a catastrophic event for neurons if blood supply to the brain (or to a portion thereof) is interrupted, as can occur during conditions such as stroke (which includes blockage of blood vessels, as well as brain hemorrhaging due to events such as rupture of an aneurysm) or cardiac arrest (cessation of the heart beat). Inadequate blood supply is called "ischemia," which implies lack of both oxygen and glucose. A closely-related condition called "hypoxia" (inadequate oxygen supply) occurs whenever ischemia occurs; however, hypoxia can also occur under certain other conditions as well, even though an adequate amount of blood is flowing to the brain, if the blood is not carrying enough oxygen, such as during suffocation or carbon monoxide poisoning. Since these two conditions are closely related, they are often referred to collectively either as ischemia, or as hypoxia/ischemia.

Yet another condition which involves inadequate energy supply to the brain can arise when not enough glucose is present in the blood (hypoglycemia). This condition can be treated by adding glucose to the blood, such as by intravenous injection in severe cases. Therefore, it usually is not of substantial concern to neurologists trying to develop ways to treat hypoxia/ischemia.

During hypoxic/ischemic conditions, the transport system which normally clears glutamate out of the synaptic fluid and pumps it back inside the neurons lacks the energy it requires to drive the system. When that happens, glutamate molecules begin to accumulate at abnormally high levels in the vicinity of EAA receptors on the surfaces of neurons. Continuous receptor activation causes the neuron to quickly reach an over-stimulated condition; it is being given repeated and incessant excitatory signals at its EAA receptors, and it interprets those signals as commands to release its own glutamate molecules at its own synaptic contacts with other neurons, which in turn excites additional neurons that were not initially affected. The process takes on an uncontrollable, runaway condition, which is aggravated even more by the fact that overexcited neurons begin consuming even more oxygen as they try to cope with the increased metabolic demands being placed on them; this further reduces the oxygen content of any nearby blood or other fluids.

This process, which is called excitotoxicity, can lead to the death of the organism, or, in people or animals that survive, to widespread and irreversible neuronal death that can extend well beyond the regions that are directly affected by a localized blockage of an artery in the brain. The same molecules which function in an absolutely vital and necessary manner as neurotransmitters in a healthy brain can turn into deadly toxins in an injured brain.

To make matters even worse, the process of excitotoxicity (which is used to indicate that neurons are actually dying, rather than merely suffering stress) cannot be reversed or arrested by restoring blood flow to the affected region of the brain; instead, the damage often increases sharply when oxygen is reintroduced after a period of hypoxia. During hypoxia, certain metabolites and enzymes can accumulate which, when the hypoxia ends, convert oxygen into a highly reactive free radical known as superoxide ($O_2^-$). Superoxide can attack and alter any molecule, and it also promotes the release of iron ions from ferritin, which in turn promotes a process called "lipid peroxidation" which destroys cell membranes.

There are numerous review articles and entire books which have been devoted entirely to discussions of efforts to prevent or control the damage caused by stroke, cardiac arrest, and other hypoxic/ischemic events and processes. Recent review articles include Whisnant et al 1990; Krause et al 1988; Meyer et al 1987; Hossmann 1985; and Wauquier et al 1987. An important series of books, entitled *Pharmacology of Cerebral Ischemia*, is issued each year shortly after a major international conference devoted entirely to cerebral ischemia; see Krieglstein 1989, and Krieglstein and Oberpichler 1990; also see Cavalheiro et al 1988. In addition, several scientific journals are entirely or predominantly devoted to experimental results related to stroke and cerebrovascular disease, including journals such as *Stroke, Journal of Cerebral Blood Flow and Metabolism, Cerebrovascular Brain Metabolism Review*, while other journals such as *Brain Research, Journal of Neuroscience, Journal of Neurochemistry*, and *Neurology* publish even more articles which directly relate to neurological hypoxia and ischemia.

Considerable effort has been devoted to various therapeutic approaches aimed at preventing glutamate which has been released by neurons, and which is accumulating at dangerous levels in synapses, from stimulating neighboring (postsynaptic) neurons to death. This approach is based on blocking activity at EAA receptors, using NMDA antagonists such as MK-801 (dizocilpine; see, e.g., U.S. Pat. No. 4,888,347, Woodruff et al 1989), dextromethorphan (see U.S. Pat. No. 4,806,543, Choi 1989), or CPP (Boast 1988), non-NMDA antagonists such as NBQX (Sheardown et al 1990) or GYKI-52466 (Tarnawa et al 1990), or mixtures of drugs which can block both NMDA and non-NMDA receptors (European patent application EP-0424 179 A2, Olney 1991).

Although these drugs have varying degrees of effectiveness in certain animal models of stroke, they suffer from several major drawbacks, including: (1) NMDA antagonists cause toxic side effects (Olney et al 1989) which can be overcome only by administering additional agents that affect additional classes of receptors (Olney et al 1991); (2) a highly effective and selective NMDA antagonist gave promising early results but was subsequently shown to offer no protective benefit in models of stroke involving larger animals; see Michenfelder et al 1989, Buchan and Pulsinelli 1990, and Lanier et al 1990; and, (3) any competitive antagonists may have to be used in very high doses, because they must compete for receptor binding sites against glutamate molecules that are already present in abnormally high concentrations in the synapses.

The situation involving post-synaptic EAA receptors is rendered even more complex and difficult to decipher since there is sharp disagreement over which EAA receptors must be blocked in order to provide effective protection against excitotoxicity. For example, U.S. Pat. No. 4,806,543 (Choi 1989) asserts that only NMDA receptors must be blocked, while Sheardown et al 1990 asserts that only non-NMDA receptors must be blocked. A third assertion that contradicts both of those positions is set forth in European patent application EP-0-424 179 A2 (Olney 1991), which asserts that both NMDA and non-NMDA classes of receptors should be simultaneously blocked.

Perhaps the single best indicator of the conflicts and contradictions that confront neuroscientists trying to reduce ischemic damage by blocking post-synaptic EAA receptors resides in the fact that the Merck drug company invested many years of effort and tens of millions of dollars into its NMDA antagonist MK-801, only to abandon MK-801 in the early 1990's.

By contrast, the subject invention focuses on an entirely different set of molecular mechanisms which involve presynaptic N-type calcium channels rather than post-synaptic EAA receptors.

Calcium and N-Channels

Calcium ions have long been known to play an important role in glutamate release by neurons; in general, calcium uptake into a neuron is a necessary step in a series of steps which results in the release of glutamate by the neuron. For general information on recent research involving calcium channel blockers, see Krieglstein and Oberpichler 1990, particularly the chapters by Siesjo et al (pp. 79–88) and Rami et al (pp. 123–128), and the collection of chapters in pages 283–315, as well as an earlier review article, Miller 1987.

Calcium is taken into neurons by at least three types of channels, which are called N, L, and T channels (Nowycky et al 1985). These three classes can be distinguished from each other in cell culture experiments by the fact that different drugs bind to different classes of receptors with varying strengths; certain types of dihydropyridines bind to L-channels but not to T or N channels, while a certain type of fast-acting poison called omega ($\omega$) conotoxin, used in nature by marine snails of the genus *Conus* to catch and kill fish, binds very tightly to N-channels, less tightly to L-channels, and even less tightly to T-channels (Kasai et al 1987).

All three types of $Ca^{++}$ channels exist on the surfaces of neurons, but not in the same locations. In neurons, L-channels and T-channels (which also exist on other types of cells such as muscle cells and pituitary cells) are located on the main body of the neuron and its finger-like dendritic processes (which are fibrils which transmit nerve impulses from a synapse to the main body of the neuron). Both L and T channels can be regarded as post-synaptic channels. They do not directly affect the release of glutamate into a synaptic junction; instead, they are involved in other neuronal functions, such as in determining how the cell will respond after it receives a nerve impulse.

A substantial amount of research has been devoted to testing various drugs (including various dihydropyridine derivatives) which block L-channels, such as flunarizine, nicardipine, and nifedipine, to determine whether they can reduce neuronal damage due to ischemia. Although these drugs are known as "calcium channel blockers," the results in tests to evaluate their protection against ischemic neuronal damage have been inconsistent. It is suspected that any beneficial effects they may have may be due to (1) vasodilating (i.e., blood vessel dilating) effects, which in some animal models can provide more blood to a brain region that is being experimentally deprived of blood flow; and (2) reduction in the formation of highly reactive oxygen radicals. It should be emphasized that these so-called calcium channel blockers suppress activity at an entirely different type of calcium ion channel, known as the L-channel, which is not a pre-synaptic channel and which has no known direct effect on excitotoxic glutamate release at synapses.

In contrast to L-type calcium channels, N-type calcium channels can be regarded as pre-synaptic neuronal calcium channels. They exist on the surfaces of synaptic "boutons" on neurons; during nerve signal transmission, glutamate is released from these neuronal boutons, in a manner that is mediated by calcium flow into neurons via N-type channels. If calcium flow into certain neurons is suppressed, then the release of glutmate by the neurons is also suppressed.

The discovery that omega conotoxin binds very tightly to N-channels (and less tightly to L-channels and T-channels) has led to at least one effort to develop drugs which can suppress glutamate release (and thereby suppress excitotoxic brain damage) by means of suppressing calcium entry into neurons through N-channels. That effort is described in a patent application published under the Patent Cooperation Treaty (PCT), number WO-91/07980 (invented by Miljanich et al, assigned to Neurex Corporation of Menlo Park, Calif.). The drugs described therein are peptide segments, containing about 25 to 20 amino acid residues, derived from the amino acid sequence of the omega conotoxin. These conotoxin-derived peptides do not bind as tightly to N-channels as the natural conotoxins; therefore, they can inhibit the uptake of calcium through neuronal N-channels without irreversibly shutting down the N-channels and poisoning or paralyzing the animal.

However, conotoxin-derived peptides suffer from various limitations which render them less than ideally useful to prevent brain damage, either due to stroke or due to progressive neurological diseases. Since they are peptides, they are degraded in the digestive tract, so oral administration is either completely infeasible, or at least difficult and inefficient. In addition, since they are relatively small peptides, they tend to be degraded or otherwise absorbed or eliminated fairly rapidly, and they might cause immunogenic reactions, if they are injected into the bloodstream. In all in vivo examples except one, the Miljanich application described peptides which were injected via "intracerebroventricular" (ICV) route, i.e., the skull bone of each rodent was surgically exposed, and the needle tip was pushed directly through the skull (apparently without using a burr hole) and through the brain tissue until the tip reached one of the ventricles near the center of the brain which hold cerebrospinal fluid.

To avoid the need for injecting drugs through the skull and directly into the brain, and to avoid the problems that arise when small foreign peptides are injected into the blood (which include potential immunologic and allergic reactions and rapid elimination or degradation of the peptide), it would be preferable if other types of N-channel blockers which are not peptides, and which are relatively stable in the blood, and which penetrate mammalian blood-brain barriers, could be developed.

It has been known for a number of years that certain types of antibiotics known as aminoglycosides (discussed below) suppress the transmission of neuromuscular signals, resulting in clinical symptoms such as respiratory depression and muscle weakness, particularly in patients under anesthesia or who are suffering from diseases such as myasthenia gravis (Sande and Mandell 1985; Pittinger and Adamson 1972; Caputy et al 1981; Miller et al 1987). Although much of the neuromuscular suppression effect is believed to be due to the suppression of acetylcholine release by cholinergic neurons, it was shown in 1977 that one type of aminoglycoside, neomycin, inhibits the pre-ganglionic nerve-stimulation-induced accumulation of $Ca^{++}$ in isolated rat ganglia, which are neurons that exist primarily in the peripheral nervous system rather than inside the CNS (Wright and Collier 1977). Subsequently, it was shown, using competitive conotoxin-binding assays, that a number of aminoglycosides do in fact bind to N-channels (Knaus et al 1987).

Neither Knaus et al 1987, nor any of the other articles on aminoglycosides, made any suggestion that aminoglycosides might be useful as therapeutic agents to protect against excitotoxicity. Despite the finding that aminoglycosides do in fact bind to N-channels, which was publicly known years ago, it appears that no researchers, prior to the Applicant, ever made any effort to determine whether aminoglycosides might be useful as neuroprotective drugs to protect against excitotoxicity.

One of the factors which strongly mitigates against the use of aminoglycosides as neuroprotective agents is that they are generally regarded as neurotoxic. For example, Knaus et al 1987 specifically refers to these drugs as "Neurotoxic aminoglycoside antibiotics" and the *Physician's Desk Reference* warns that, "Patients treated with [injectable] aminoglycosides should be under close clinical observation because of the potential toxicity associated with their use" (1990 edition, page 1981). Aminoglycosides reportedly can destroy kidney functioning and can cause other problems including "ototoxicity" (which involves the ear and which can lead to problems such as vertigo, dizziness, loss of hearing, induction of a ringing or roaring sound in the ears, etc.). Aminoglycosides can also cause undesired reactions when combined with a number of other drugs. Accordingly, although they are quite safe and effective when used as topical ointments on the skin, they have a reputation which indicates that they should not be used in formulations that enter the bloodstream unless a patient is kept under careful observation.

Another factor that probably has discouraged research into aminoglycosides as potential agents to prevent or reduce excitotoxic brain damage is that they are generally presumed not to penetrate the mammalian blood-brain barrier. The tests discussed in articles such as Knaus et al 1987 and Miller et al 1987 all involve tissue culture tests (which involve isolated neurons cultured in dishes in nutrient solutions) or neurons in the peripheral nervous system (which are not protected by any structures comparable to the blood-brain barrier).

It should also be noted that Knaus et al 1987 did not address the problem of conotoxin binding to L-type or T-type calcium channels. Knaus et al showed that aminoglycosides do not bind in significant quantities to L-channels, in experiments which involved competitive binding assays using radiolabelled L-channel blocking agents and aminoglycosides; however, Knaus et al did not address the problem of conotoxin binding to L-channels, which is substantial (Kasai et al 1987) and which aminoglycosides cannot prevent. This problem can be overcome, today, by using a non-labelled L-channel blocker during the conotoxin binding assays; the L-channel blocker will occupy the L-channel sites and inhibit the conotoxin from binding to the L-channels. However, that step apparently was not utilized by Knaus et al. Accordingly, the results described in Knaus et al must be regarded as skewed by conotoxin L-channel binding.

For these and possibly other reasons, there has not been, to the best of the Applicant's knowledge, a single publication or patent which discusses or proposes the use of aminoglycosides as calcium uptake inhibitors to prevent or reduce brain damage due to stroke, cardiac arrest, or other hypoxic or ischemic events.

However, the risk of potentially toxic side effects, which appear formidable in the various warnings, are actually quite manageable, particularly when a patient is already being carefully treated and monitored in a hospital setting during a crisis event such as a stroke. Aminoglycosides were used for many years on millions of patients, with a high degree of effectiveness and complete safety in the large majority of patients. The problems of kidney toxicity are relatively small if the patient's kidneys are healthy when the treatment begins, and the risk of ototoxicity can be minimized or avoided entirely by administering an aminoglycoside only for a short period of time, and by monitoring the patient for any early warning signs of ototoxicity.

In light of these factors, aminoglycosides can be administered safely and effectively to prevent excitotoxic brain damage, provided that such use is done by a skilled physician who carefully supervises the patient.

Accordingly, one object of the subject invention is to disclose that aminoglycoside compounds which have been extensively tested and proven to be safe as antibiotics are capable of preventing or reducing neuronal injury or death due to ischemic/hypoxic events such as stroke or cardiac arrest, and to other events or conditions that cause excitotoxic damage to neurons, such as epileptic seizures and possibly some types of progressive neurodegenerative diseases.

Another object of this invention is to disclose the correlations between certain types of in vitro tests involving isolated cells or tissue specimens, and in vivo results showing protection against brain damage in intact adult mammals when aminoglycosides are used.

SUMMARY OF THE INVENTION

This invention provides a method of reducing excitotoxic damage to neurons, which can occur as a result of ischemia or hypoxia (such as during or after a stroke or cardiac arrest) or as a result of various other events or conditions such as an epileptic seizure or certain types of poisoning. This method involves the administration of a therapeutically effective amount of an aminoglycoside which suppresses the flow of calcium ions into neurons through presynaptic N-type calcium channels. Such aminoglycosides must suppress calcium ion flow at a potency higher than the potency of streptomycin, which has moderate N-channel blocking potency. Various commercially available aminoglycosides, such as neomycin and Gentamicin, have been shown to suppress calcium uptake through N-channels with substantially higher levels of potency. By inhibiting calcium uptake in pre-synaptic regions, they can suppress the synaptic release of glutamate, a neurotransmitter which can kill neurons under excitotoxic conditions.

Aminoglycosides have been tested in a variety of assays, including (1) in vitro tests using homogenized brain cell preparations, to evaluate binding activities at N-channels on the cell membranes; (2) in vitro tests using hippocampal tissue slices to evaluate recovery of neuronal activity in such tissue slices after a period of oxygen deprivation; (3) in vivo tests to evaluate the ability of various aminoglycosides to control seizure activity in intact adult mammalian animals; and (4) in vivo tests on intact adult mammalian animals to evaluate the ability of various aminoglycosides to block brain damage due to surgically induced global ischemia. The results gathered to date indicate that (1) aminoglycosides which are more potent than streptomycin in blocking ion flow through N-type calcium channels are effective in significantly reducing damage caused by ischemia in the brains of adult mammalian lab animals without causing undesired behavioral side effects, and (2) the effectiveness of all BBB-permeable aminoglycosides tested to date in preventing excitotoxic brain damage is directly correlated with their potency in suppressing N-channel activity. In addition, evaluation of the chemical structures of these aminoglycosides indicates that there is a correlation between the number of primary amino groups on an aminoglycoside, and its potency as an N-channel blocker and as a neuroprotective agent.

A screening test is also disclosed which is based on the discovery of N-channels on blood platelet cells. Blockade of ADP-induced platelet aggregation correlates with N-channel blocking activity and with conotoxin-binding inhibition. The platelet assay provides a simple, rapid, convenient and inexpensive screening test that can quantify the potency of candidate drugs in suppressing N-channel calcium uptake, without requiring the testing on neurons in cell culture.

DESCRIPTION OF THE PREFERRED EMBODIMENTS

Figure 1:
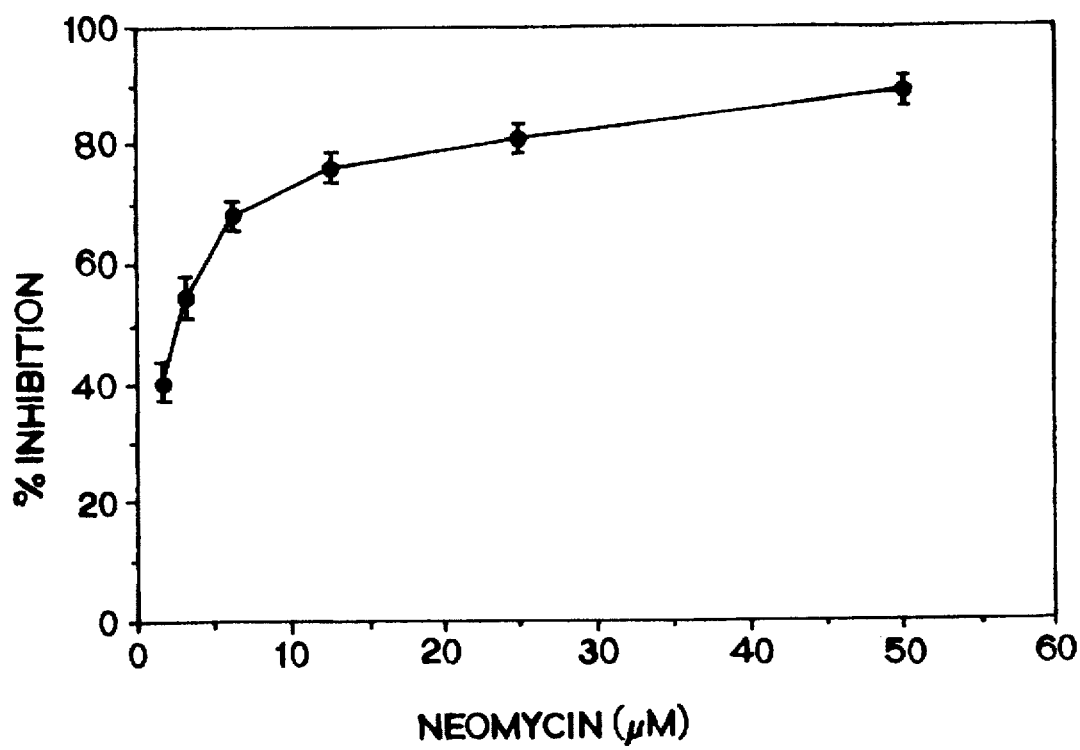
FIG. 1 depicts the inhibition by neomycin of omega conotoxin binding to N-channels in brain cell membrane fragments (Example 1).

This invention provides a method of reducing excitotoxic damage to neurons, which can occur as a result of ischemia or hypoxia (such as during or after a stroke, cardiac arrest, or heart attack) or during various other events or conditions such as an epileptic seizure or certain types of poisoning or neurodegenerative diseases which have excitotoxic components. This method involves administering, to a patient suffering or at risk of excitotoxic neuronal damage, a therapeutically effective amount of an aminoglycoside that is capable of suppressing the uptake of calcium ions by neurons through presynaptic N-type $Ca^{++}$ channels (for convenience, these are referred to herein as N-channels).

The suppression of calcium uptake by neurons, via aminoglycoside blockage of neuronal N-channels, reduces the extent to which the affected neurons become depolarized and excited or stimulated. As noted in the Background section, the "resting" state of neurons is a polarized state, with steep ion gradients across the cell membrane. By blocking N-channels and reducing the flow of calcium ions into neurons through those ion channels, certain aminoglycosides can suppress the excitatory stimulation of neurons. This in turn reduces the synaptic release of glutamate by the neurons. As noted previously, glutamate is an excitatory neurotransmitter that can become lethal to neurons under excitotoxic conditions, such as during a stroke or cardiac arrest.

Tests have shown that only certain types of aminoglycosides are effective in suppressing activity at N-channels. Accordingly, the invention and the claims are limited to those aminoglycosides which are, in fact, effective in suppressing N-channel activity. This effectiveness is determined by referring to streptomycin as a "benchmark" compound. Streptomycin has some activity as an N-channel blocker, but its potency is relatively low, and it was shown to be ineffective in reducing hypoxic damage to hippocampal tissue slices except when administered in high dosages. By contrast, various other aminoglycosides (including neomycin B,C, gentamicin, and sisomicin) were shown to be substantially more potent than streptomycin, both in blocking N-channel activity and in protecting neurons against hypoxic or ischemic damage. A mixture of neomycin B and neomycin C, which are isomers of each other, is referred to herein as neomycin B,C.

Several in vitro screening techniques are disclosed herein for quantitatively evaluating the potency of any candidate aminoglycoside in blocking the flow of calcium ions through N-channels, and data is provided below on the potency of a substantial number of aminoglycosides, in Table 2. In addition, a direct relation has been noted on aminoglycosides tested to date, between the number of primary amino groups on an aminoglycoside, and its potency as an N-channel blocker.

Accordingly, streptomycin is used herein to establish a boundary between effective and ineffective aminoglycosides, regarding their use as neuroprotective drugs. This invention, and the claims below, are limited to the use of aminoglycosides that are more potent than streptomycin in blocking the flow of calcium ions through N-type calcium channels in neurons.

Using a selected aminoglycoside as an N-channel blocker to suppress the release of glutamate (or aspartate) into the synaptic fluid between two neurons during an excitotoxic event offers a direct method of reducing the amount of excitatory neurotransmitters released by neurons. By contrast, most of the research in the field of trying to reduce brain damage due to stroke involves other types of drugs (mainly NMDA antagonists such as MK-801, and non-NMDA EAA antagonists such as quinoxalinediones) which are being studied in the hope that they can provide a way to block the excitotoxic effects of glutamate molecules which have already been released by neurons, and which have already entered the synaptic fluid and are repeatedly activating EAA receptors and wreaking havoc in the CNS. Clearly, a preventive approach which reduces the release of an endogenous excitotoxin is preferable in several respects to an approach which tries to reduce the damage being caused by excitotoxins that have already been released.

It should also be noted that efforts to block selected types of EAA receptors using NMDA or non-NMDA antagonists tend to offer effective protection only for limited regions of the brain, or for specific cell types in the brain, since different types of neuron and different regions of the brain have varying concentrations of different types of EAA receptors. By contrast, to the best of the Applicant's knowledge, N-channels exist on the pre-synaptic surfaces of all neurons that transmit nerve signals by synaptic release of excitatory amino acids. Therefore, this invention appears capable of offering some degree of protection against EAA-mediated neurons throughout the entire brain. Such protection can be referred to as "global protection," since it is distinct from the type of "focal" protection offered by NMDA or non-NMDA antagonists which protect only certain regions of the brain having neurons with high concentrations of certain types of EAA receptors.

If an anti-excitotoxic N-channel blocking aminoglycoside as described herein is intended for use to protect neurons in the central nervous system, it must be able to penetrate a mammalian blood-brain barrier (BBB) in therapeutically effective quantities. As described below, the ability to penetrate mammalian BBB's and provide protection for the brain, after injection into the peritoneal cavity, has been demonstrated for certain aminoglycosides in in vivo experiments.

The terms "aminoglycoside" and "aminosaccharide" are used according to their conventional chemical meanings, as described in various standard texts on organic chemistry. The following is a condensed summary of these terms, to be interpreted in light of more extensive reference works.

As implied by the term, an aminosaccharide is a saccharide molecule (the term saccharide is used interchangeably with sugar) having at least one amine group coupled to it, either directly or indirectly. Saccharide molecules (i.e., polyhydroxylated aldehydes or ketones) exist as both straight chains and ring structures, which spontaneously convert back and forth between straight and ring forms in an equilibrium-type "tautomeric" mode. Since the equilibria between straight and ring structures tends to generate more ring structures than straight chains at any given moment when dissolved in an aqueous solvent, most saccharides are usually drawn and discussed as ring structures.

Saccharide rings are called furanose rings if the ring structure itself (excluding any pendant groups) contains five atoms, and pyranose rings if the ring contains six atoms. Most furanose molecules are derived from pentose sugars (i.e., sugars which contain five carbon atoms, such as ribose, arabinose, or xylose). In a pentose molecule, one of the atoms in the ring form of the molecule is an oxygen atom; the fifth carbon atom is attached to the ring in a pendant structure, usually as a hydroxylated methyl group.

In the same manner, most pyranose molecules (with six-membered rings) are hexose sugars such as glucose, galactose, and mannose, or derivatives thereof. Hexose sugars contain six carbon atoms; in the most common pyranose ring, five carbons are in the ring along with an oxygen atom; the sixth carbon atom is attached to the ring in a pendant group.

A glycoside molecule contains at least one saccharide component (usually drawn as a ring) attached through an oxygen atom (which can be regarded as an ether linkage) to a second molecular group having at least one carbon atom. If a glycoside molecule is chemically hydrolyzed to break the ether linkage(s), it will release at least one saccharide molecule. Usually, the glycoside linkage is between adjacent saccharide rings, to form disaccharides, trisaccharides, polysaccharides, etc.

As implied by the name, an aminoglycoside is a glycoside with one or more amino groups. Because of their biological properties, aminoglycosides are an important class of aminosaccharides. Neomycin A (neamine), Neomycin B and C, Gentamicin, sisomycin, streptomycin, and tobramycin are all aminoglycosides, since they have the requisite amine groups, saccharide rings, and oxygen linkages. Most aminoglycosides were initially identified due to the antibacterial activities of various microbes that synthesize such compounds in nature. Many of these aminoglycoside antibiotics can be altered or derivatized in various ways that do not destroy their functioning as antibiotics; for example, if Neomycin B or Neomycin C is cleaved between the disaccharide structure and the pentose ring, the two cleavage products are Neomycin A (a disaccharide, also known as neamine) and either Neobiosamine B or Neobiosamine C.

Some compounds are occasionally called aminoglycosides even though they do not have a glycosidic oxygen linkage, since they are components of larger molecules which are true aminoglycosides, and they are commonly synthesized using bacterial aminoglycosides as starting reagents. Examples include 2,6-diamino-2,6-dideoxy-D-glucose (which can be obtained by hydrolyzing Neomycin) and streptidine (which can be obtained by hydrolyzing streptomycin). Since these aminosaccharide compounds do not have the glycosidic oxygen linkage and are not true aminoglycosides under proper chemical terminology, they are excluded from the subject invention and from coverage by the claims herein, which are limited to true aminoglycosides. However, it is recognized that certain types of non-glycosidic aminosaccharides may have the same type of N-channel blocking activity as various aminoglycosides. Accordingly, an effort will be made to screen various non-glycosidic aminosaccharides (particularly those having numerous primary amine groups) as described herein, in an effort to identify one or more which have N-channel blocking activity without having other adverse side effects, and it should be recognized that this invention, in its broadest sense, is based on the realization that certain aminosaccharides which have N-channel blocking activity can function as effective neuroprotective agents to reduce excitotoxic damage, with minimal adverse side effects.

It is also recognized that in certain conditions, particularly involving long-term administration of an aminoglycoside (such as in treatment of people suffering from epilepsy or excitotoxic neurodegenerative diseases), it would be preferable to use N-channel blocking aminoglycosides which do not have high levels of antibiotic activity. Such compounds could protect neurons against excitotoxic damage, without raising concerns about alterating normal microbial flora in the body or promoting the growth and spread of antibiotic-resistant strains of bacteria. Accordingly, although the testing to date has involved antibiotic aminoglycosides (since they are easily commercially available and do not need to be custom-synthesized), an effort will be made to identify or synthesize other aminoglycosides or aminosaccharides that do not have high levels of antibiotic activity.

Based on structural similarities between the various antibiotics that have been found to block activity at N-channels, it is believed that the best candidates for screening tests to identify analogs and derivatives may which have improved N-channel binding characteristics are likely to contain at least one saccharide ring having at least five carbon atoms (i.e., a furanose or pyranose ring), and at least two and preferably more primary amine groups (i.e., amine groups in which the nitrogen atom is coupled directly to only one carbon atom; by contrast, in secondary amine structures, the nitrogen atom is coupled to two carbon atoms, and in tertiary amines, the nitrogen atom is coupled to three carbon atoms). The correlation between the number of primary amine groups and the potency of N-channel blocking activity is shown in Table 1, which lists the number of primary and secondary amino groups on each of the tested aminoglycosides. These numbers are based on chemical structures published in reference works such as *The Merck Index*.

TABLE 1

CORRELATION OF PRIMARY AMINO GROUPS
WITH N-CHANNEL BLOCKING POTENCY

| Aminoglycoside | Primary A's | Secondary A's |
|---|---|---|
| Neomycin (most potent) | 6 | 0 |
| Sisomicin (high potency) | 6 | 0 |
| Gentamicin (intermediate) | 4 | 1 |
| Streptomycin (low potency) | 2 | 4 |

Although this correlation will need further evaluation, it appears to offers a simple structural indicia which suggests whether any candidate aminoglycoside or other aminosaccharide deserves high priority in screening tests to evaluate its potency as an N-channel blocker.

A variety of in vitro as well as in vivo tests have been carried out which clearly show the correlation between N-channel blocking potency, and actual neuroprotective effects in living, intact animals. These tests, describes in detail in the examples, include the following:

(1) in vitro tests described in Examples 1 and 2, involving membrane fragments from rat or human brain cells, using competitive binding assays to determine which aminoglycosides are most potent in blocking the binding of a high-affinity peptide (omega-conotoxin) to N-channels. These tests identified neomycin, gentamicin, and sisomicin as the most potent N-channel blockers, and streptomycin as a somewhat less potent N-channel blocker. These four aminoglycosides became the primary candidates in subsequent hippocampal tissue tests.

(2) tests described in Example 3, involving perfused slices of hippocampal tissue from sacrificed rats. The four aminoglycoside candidates with the highest N-channel blocking potency were tested to determine their ability to protect the hippocampal neurons against damage during and after a period of hypoxia. The aminoglycosides all showed neuroprotective effects, as evidenced by the ability of treated neurons to continue firing normally after oxygen was resupplied to the tissue slices. Streptomycin was only marginally effective and required high doses; accordingly, it was chosen as a benchmark compound, and the claims have been limited to aminoglycosides which have greater N-channel blocking potency than streptomycin.

(3) in vivo tests using surgically-induced ischemia in gerbils, described in Example 4. The two aminoglycosides (neomycin and gentamicin) which showed the best protective effects in the hippocampal slice tests were tested and shown to provide good protection against actual ischemia in adults in a mammalian species which is widely used and accepted in anti-ischemia research.

(4) in vivo tests described in Examples 5–7, using aminoglycosides to protect adult rats and mice against seizures and excitotoxic damage induced by convulsant drugs or electroshock treatment. These tests showed that aminoglycosides can provide comparable or better protection than diazepam (widely sold and used under the trademark VALIUM), an anxiolytic drug that is widely used in research as an anti-convulsant drug, without causing the animals to display the undesired behavioral side effects associated with diazepam.

The ability of aminoglycosides to suppress seizures in convulsant-treated animals without otherwise altering the behavior of the animals is an important and highly positive result. It indicates that suppression of excessive neuronal activity due to N-channel blockade does not disrupt other normal and desirable neuronal activities and functions.

It should also be noted that the aminoglycosides tested were found to be effective in protecting against brain damage, when injected into the peritoneal (abdominal) cavities of test animals. This confirms the ability of these aminoglycosides to penetrate the mammalian blood-brain barrier (BBB), which is essential in providing convenient and useful routes of administration (such as intravenous injection) that do not require injection of the protective drug through a hole drilled into the skull, directly into a brain ventricle.

In addition, all of the data gathered to date show a direct correlation between potency in blocking calcium ion flow through N-channels, and potency in protecting neurons against excitotoxic damage. Based on the results gathered to date, and on an understanding of the neuronal processes which are involved during calcium-mediated neuronal stimulation-depolarization and during the subsequent release (by over-stimulated neurons) of excessive quantities of glutamate and aspartate, which become deadly endogenous neurotoxins under hypoxia, ischemic, and other excitotoxic conditions, it is believed that anti-excitotoxic neuroprotective effects of aminoglycosides are due directly to their ability to suppress activity at N-channels. This N-channel blocking activity allows certain aminoglycosides to suppress and control excessive neuronal activation, which in turn controls and reduces the release of potentially excitotoxic neurotransmitters. By showing a direct correlation between N-channel blocking potency and neuroprotective efficacy, this invention discloses a clear and direct correlation between an easily measured in vitro activity which can be determined for any candidate compound using routine screening tests, and an extraordinarily valuable therapeutic benefit for patients suffering or at risk of excitotoxic brain damage.

For acute indications such as stroke, cardiac arrest, or head trauma, aminoglycosides which control N-channel activity may be administered by injection, either via single-injection bolus or via continuous infusion. Typical dosages will be in the range of about 2 to about 20 mg/kg intravenously (IV) immediately or as soon as possible after the establishment of reperfusion (within 3 hours). Doses administered by bolus injection can be repeated at 6–12 hour intervals for several days after the acute event. Alternately, administration may be by direct infusion into the brain. For example, if a patient is undergoing brain surgery to repair a burst aneurysm or remove a brain tumor, a cannula can be emplaced in the brain which will deliver a neuroprotective aminoglycoside directly to the affected region or into a cerebral ventricle. If desired, the cannula can be attached to an osmotic mini-pump, or to an implanted slow-release device which can use (for example) a polymer sold under the trademark ELVAX (DuPont Company, Wilmington, Del.), which releases the compound slowly over a sustained period.

Aminoglycoside drugs as described herein can also be used for neuroprotection purposes in patients undergoing surgery, such as cardiac surgery where the patient must be placed on cardiopulmonary bypass (a so-called heart-lung machine), or when patients are undergoing endarterectomy to remove plaques from the insides of arterial walls. The drug can be administered in sterile saline via the intravenous route starting 30 minutes before the surgery. The infusion rate is at a rate of between 0.1 to 1.0 mg/kg/minute and is continued for the duration of the procedure. The drug decreases the degree and extent of neurological damage resulting from the ischemia induced by the surgical procedure. Neurologic status post surgery is assessed by standard cognitive function tests.

Administration to experimental animals can be either intravenous or intraperitoneal at doses ranging from 0.25 to 100 mg/kg. The preferred dose is between 0.5 and 5 mg/kg. The dosing is done before the induction of ischemia or up to 1 hour afterwards and repeated at 3 hours and 12 hours post-reperfusion.

For most aminoglycosides, oral administration is very inefficient. Accordingly, for longer-term treatment of problems such as epileptic, trauma-induced, or other seizures, or for treating neurodegenerative diseases which involves excitotoxic overstimulation of neurons as a component of the disease, implantation of a slow-release device (such as an osmotic mini-pump) is preferable if an aminoglycoside is used which is not readily absorbed into the blood through the intestinal walls. Alternately, oral administration of certain types of aminoglycosides may be feasible if appropriate enhancement techniques are used, such as using enteric coatings to prevent hydrolysis in the stomach, and coupling the desired chemical structure to a carrier molecule or pro-drug form that increases absorption into the blood after oral ingestion.

In addition to specific aminoglycosides discussed herein, salts or isomers of such aminoglycosides can be used, provided that they are both pharmaceutically acceptable, and therapeutically effective when used as described herein. The term "pharmaceutically acceptable" embraces those characteristics which make a drug suitable and practical for administration to humans; such compounds must be sufficiently chemically stable under reasonable storage conditions to have an adequate shelf life, and they must be physiologically acceptable and capable of penetrating the blood-brain barrier when introduced into the bloodstream. Acceptable salts can include alkali metal salts as well as addition salts of free acids or free bases. Examples of acids which may be employed to form pharmaceutically acceptable acid addition salts include inorganic acids such as hydrochloric acid, sulphuric acid and phosphoric acid, and organic acids such as maleic acid, succinic acid and citric acid. Alkali metal salts or alkaline earth metal salts might include, for example, sodium, potassium, or magnesium salts. All of these salts may be prepared by conventional means. The nature of the salt is not critical, provided that it is non-toxic and does not substantially interfere with the desired activity.

EXAMPLES

EXAMPLE 1

IN VITRO TESTS FOR N-CHANNEL BLOCKING ACTIVITY, USING CONOTOXIN BINDING ASSAYS

Numerous aminoglycosides were tested to quantify their ability to suppress calcium flow through N-type calcium channels, using in vitro tests that evaluates the ability of test compounds to inhibit conotoxin binding to synaptic membrane fragments (derived from brain tissue) containing N-channel receptors. Suitable protocols for preparing synaptic membranes fragments have been published (see, e.g., Ferry et al 1984). If desired, the excised brain tissue can be from a brain region which is known to have high concentrations of one or more specific types of EAA receptor.

These tests were carried out as follows. Brain tissue was used from rats or mice that had been anesthetized with halothane and decapitated. Membrane fractions were prepared as follows. Tissue samples were mixed with 25 tissue-volumes of 50 mM Tris-HCl buffer, pH 7.5. Tissue-buffer mixtures were homogenized using a Brinkman Polytron homogenizer, and resulting tissue homogenate was centrifuged at 2,400 g to pellet non-membrane derived material. The supernatant containing the brain membrane fragments was centrifuged at 30,000 g in a refrigerated (4° C.) centrifuge for 20 minutes. The pellet was resuspended in 100 tissue-volumes of the Tris-HCl buffer and centrifuged again as above. The process was repeated two more times, and the resulting pellet was resuspended in Tris-HCl buffer solution. The suspended tissue contained synaptosomal and other neurally derived membrane fragments with intact N-channels.

Varying concentrations of a candidate aminoglycoside compound ranging from $10^{31\ 9}$ to $10^{31\ 4}$ molar were mixed with 12 ug (protein) of a tissue suspension and incubated for 30 minutes. This was followed by addition of $0.10\times10^{31\ 9}M$ of an omega-conotoxin containing a radioactive isotope, $^{125}$iodine (labelled conotoxin is commercially available from New England Nuclear). The mixture was incubated at 4° C. for 30 minutes, followed by rapid filtration through Whatman GF/B glass filters having a pore size of 1.0 microns and four 3 ml washes using cold Tris buffer. The washing and filtration was performed in a Brandel cell harvester. The filters were air dried and counted in a gamma counter.

Inhibition of conotoxin binding to N-channels (which indicated that an aminoglycoside being tested became bound to and occupied the N-channel molecules, thereby rendering the N-channels inaccessible to conotoxin) was reflected by decreased radioactivity on the filters. Inhibition potency is determined by plotting inhibitor concentration versus the percent of control omega conotoxin binding in the absence of inhibitor. The ability of an aminoglycoside to inhibit conotoxin binding is expressed in terms of an $IC_{50}$ value, which indicates the concentration of the aminoglycoside that inhibits conotoxin binding by 50 %. A lower $IC_{50}$ value indicates more potent N-channel blocking activity.

Binding of several aminoglycosides to the L-type $Ca^{2+}$ channel was determined by the ability of the compounds to inhibit binding of a radiolabelled (tritiated) dihydropyridine drug called PN-200, which selectively binds to and blocks activity at the L-type $Ca^{2-}$ channel. None of the aminoglycosides tested showed any significant affinity for the L-type channel.

The results of these tests are provided in Table 2.

TABLE 2

BLOCKADE OF N-CHANNELS IN BRAIN CELL FRAGMENTS

| Aminoglycoside | N-channel IC50 | L-channel IC50 |
|---|---|---|
| Amikacin | 45 µM | Not tested |
| Bekanamycin | >100 µM | No inhibition |
| Butirosin | 150 µM | Not tested |
| Dibekacin | 60 µM | No inhibition |
| Dihydrostreptomicin | >50 µM | Not tested |
| Gentamicin (mixture) | 10 µM | Not tested |
| Hygromycin B | >1 mM | Not tested |
| Kanamycin | >50 µM | No inhibition |
| Kasugamycin | >1 mM | Not tested |
| Lividomycin A | 50 µM | No inhibition |
| Neamine | 25 µM | Not tested |
| Neomycin B, C | 2.5 µM | No inhibition |
| Paromomycin | 40 µM | No inhibition |
| Ribostamycin | 150 µM | No inhibition |
| Sisomicin (Antibiotic 66-40) | 5–10 µM | No inhibition |
| Spectiomycin | >1 mM | Not tested |
| Streptomycin | 25 µM | No inhibition |
| Tobramycin | >50 µM | Not tested |
| Xylostasin | 250 µM | Not tested |

These data indicate that out of the various aminoglycosides tested, the ones with the highest N-channel blocking potencies are Neomycin B,C (2.5 µM $IC_{50}$), sisomicin (5–10 µM), Gentamicin (10 µM), and streptomycin (25 µM).

As described below, neomycin B,C, sisomicin, and gentamicin were all shown to restore orthodromic and antidromic activity in rat hippocampal tissue slices; streptomycin was also tested, and shown to some potency but at substantially lower levels. Neomycin B, C and gentamicin were subsequently tested and shown to be neuroprotective in in vivo models which surgically create actual forebrain ischemia or which measure suppression of chemically induced seizures.

Furthermore, all data gathered to date in either in vitro or in vivo experiments indicate that there is a strong and direct correlation between potency in blocking N-channels in in vitro (cell fragment) tests, protection of intact hippocampal slices in more elaborate in vitro tests, and actual neuroprotective efficacy in in vivo tests using surgical ischemia or convulsant drugs on adult mammals.

It should also be noted that it is possible to evaluate the effect of a calcium channel blocker on calcium uptake by directly measuring the quantity of calcium being taken into a neuron in the presence and absence of a candidate compound. Intracellular and extracellular calcium measurements can be performed using techniques or reagents such as patch clamping, dyes such as fura-2 and quin-2 which become fluorescent in the presence of calcium ions, or radiolabelled calcium isotopes such as $^{45}Ca$.

EXAMPLE 2

TESTS ON BRAIN TISSUE FROM HUMANS

Human cortex was used to provide membrane fragments to be used in the N-channel conotoxin binding assay, with test results compared to those obtained from rats, described in Example 1. Brain tissue was obtained within 12 h post-mortum from a medical school, and assayed using protocols similar to the protocols in Example 1. Out of all aminoglycosides tested on human tissue, no significant differences were detected between $IC_{50}$ values obtained from rat and human brain tissue.

EXAMPLE 3

TESTS ON HIPPOCAMPAL TISSUE FROM RATS

Another set of tests evaluated the ability of several selected aminoglycosides in reducing hypoxic damage in hippocampal tissue slices from rats. The aminoglycosides selected for hippocampal tissue tests had shown relatively high potency in suppressing activity at N-channels, in initial tests involving omega-conotoxin binding to neuronal membrane fragments, as described in Example 1. The hippocampal slice assays were sponsored and funded by the Applicant, and were carried out at the UCLA Medical Center in Los Angeles by an independent investigator.

This assay used intact slices of hippocampal tissue from the brains of sacrificed rats. Tests using perfused tissue slices are often used in neurology, since intact, cohesive tissue often provides a better model of in vivo cell and tissue behavior than broken cell fragments or isolated cells cultured under artificial conditions. If properly perfused, so-called "CA1" neurons in hippocampal tissue slices will generate electrophysiological responses (which can be measured quickly and easily, using a device comparable to an electroencephalograph) for several hours. Accordingly, if a candidate neuroprotective drug can prolong, restore, or otherwise increase the ability of neurons in perfused tissue slices to generate electrical spikes having normal and desirable amplitudes and frequencies (as distinct from seizure-inducing convulsant drugs, which induce spikes having abnormal amplitudes or frequencies), this provides strong and direct evidence that the candidate drug does indeed has substantial neuroprotective activity. Such tests are widely used and accepted, and are described in various references such as Whittingham et al 1984, and Schuur and Rigor 1992.

The protocols described below are described in more detail in Wallis et al 1992. Briefly, Sprague-Dawley rats were anesthetized with halothane and decapitated. The brain was quickly removed and placed in cold artificial cerebrospinal fluid (CSF) for one minute. The artificial CSF contained (in mM) NaCl, 126; KCl, 4.0; $KH_2PO_4$, 1.4; $MgSO_4$, 1.3; $CaCl_2$, 2.4; $NaHCO_3$, 26; and glucose, 4.0, with a pH of 7.4, saturated with a gas mixture of 95% $O_2$ and 5% $CO_2$. The brain was sliced to provide hippocampal tissue slices that were then placed in recording wells with the temperature of the surrounding bath thermostatically controlled to 34° C.

One hour after placement of slices into the recording wells, the orthodromic CA1 population spike (PS) was measured. This indicator of cell function was elicited by stimulation using a twisted bipolar electrode placed over the CA3 Schaffer collaterals. Responses were recorded using tungsten electrodes inserted into the pyramidal layer of CA1. Current strengths (in the stimulating electrodes) and electrode depth (for the measuring electrodes) were adjusted to obtain maximal amplitude of the CA1 spikes. Only slices having an orthodromic CA1 PS of 3 mV or greater on initial assessment were used for further testing.

In control samples, tissue slices were submerged in artificial CSF fluid that did not contain any aminoglycoside. Test samples were treated identically, but the CSF fluid contained a known concentration of an aminoglycoside drug.

The assays involved subjecting hippocampal tissue slices to hypoxic conditions for limited periods of time, and then measuring the ability of the CA1 cells to respond to electrical stimulation after that period of hypoxia. To initiate hypoxia, paired hippocampal slices (i.e., two tissue slices from the same animal) were placed in two recording wells, and the perfusion fluid to both wells was changed to artificial CSF containing no free oxygen; the CSF fluid was saturated with 95% $N_2$ (instead of $O_2$) and 5% $CO_2$. One slice in each pair additionally received exposure to an aminoglycoside.

Exposure of treated slices to an aminoglycoside began 30 minutes prior to the onset of hypoxia, and was continued until 15 minutes after the termination of hypoxia. The period of hypoxic deprivation was variable for different slices; during hypoxia, each control tissue slice (i.e., each slice that had not been contacted by the aminoglycoside) was monitored to ensure that a "hypoxic injury potential" (HIP; see Fairchild et al 1988) was still present. The hypoxic deprivation for paired slices was terminated by adding oxygen to the perfusion medium 5 minutes after the disappearance of the HIP in the untreated slice, and the two paired slices were monitored for an additional 90 minutes. Final CA1 orthodromic PS amplitude was then compared to the original CA1 orthodromic PS amplitude which had been measured prior to treatment. Antidromic PS amplitude was also assessed before hypoxia, and after 90 minutes of recovery.

Among aminoglycoside-treated slices, some slices were given electrical stimulation every 30 seconds throughout the entire perfusion period, including the hypoxic period. Those slices are referred to as stimulated slices. In unstimulated slices, no electrical stimulus was given during the hypoxic period. In stimulated slices, ongoing periodic stimulation imposes additional metabolic demands, which worsens excitotoxic injury; this provides an even more rigorous test.

Stimulated slices, which were monitored for mean PS recoveries throughout hypoxia, were analyzed using Student's t-test. Unstimulated slices, which were assessed for CA1 orthodromic and antidromic PS amplitude only at the beginning and end of experiments, were analyzed using the Wilcoxon rank-sum test. The CA1 injury produced by hypoxia in this assay was very severe in unmedicated, unstimulated slices, and showed the expected characteristics of excitotoxic neuronal injury. The functioning of post-synaptic elements, as reflected by CA1 EPSP slope and orthodromic PS, appeared to be especially sensitive to hypoxic exposure, while CA3 fiber volleys showed relative resistance in these assays.

The data gathered during these experiments showed that neomycin at 1.0 mM yielded very good protection. Stimulated slices recovered 88±5% of CA1 orthodromic and 94±0.3% of CA1 antidromic PS amplitudes. During these tests, paired unmedicated (control) slices showed poor recovery from the hypoxic treatment, with 0% of original CA1 orthodromic PS amplitude, and 15±6% (mean value plus or minus standard error) of original CA1 antidromic PS amplitudes. The antidromic protection shows that neomycin protected neuronal cell bodies and axonal elements, while the orthodromic protection indicates that synaptic function was also maintained. Neomycin at 1.0 mM also showed very good protection of unstimulated slices, yielding 102±10% orthodromic recovery and 95±4% antidromic recovery, compared to unmedicated unstimulated slice recoveries of only 6±5% and 9±6%, respectively.

Additional studies to evaluate the concentration dependency of neomycin indicated that neomycin at 0.2 mM showed no significant neuroprotection, while neomycin at 0.5 mM showed an intermediate level of protection. In stimulated slices, the neomycin $EC_{50}$ for orthodromic and antidromic PS recovery was found to be 573 μM and 458 μM. For unstimulated slices, the neomycin $EC_{50}$ for orthodromic and antidromic PS recovery was 472 μM and 448 μM.

Sisomicin at 1.0 mM provided protection near the level provided by neomycin at 1.0 mM. With sisomicin treatment, CA1 orthodromic and antidromic population spikes in stimulated slices recovered to 76±9% and 70±15%, compared to 0% and 3±2% recovery in paired unmedicated slices. Unstimulated slices treated with sisomicin showed somewhat greater protection with CA1 orthodromic and antidromic PS recovery of 93±3% and 93±3%, compared to unmedicated slices which showed recoveries of 7± 3 and 9±3%.

Gentamicin at 2.5 mM also provided substantial protection of neurons against hypoxia. In stimulated slices, gentamicin treatment produced a mean CA1 orthodromic PS recovery of 60±23 % and a mean antidromic recovery of 72±16%, while paired unmedicated slices recovered to 0% orthodromically and 4±1% antidromically. Unstimulated slices treated with 2.5 mM gentamicin displayed a mean 102±3% orthodromic CA1 PS recovery, compared to a mean 7%±3% in matched unmedicated slices. Gentamicin also provided antidromic recovery in unstimulated slices to 102±3%, while matched unmedicated slices yielded 10±4%.

Streptomycin at 10 mM (i.e. ten times higher than the 1.0 mM concentration of neomycin that provided protection) provided some degree of protection (38±22%) of CA1 antidromic population spikes; however, it did not appear to provide any protection of orthodromic spikes, and it was not regarded as adequate for providing effective neurological protection. In other tests, including tests using human brain tissue, it became moderately effective in protecting hippocampal slices when concentrations were increased to about 25 mM.

No gradual decrease in the traits used to measure the HIP was observed in slices treated with aminoglycosides other than sisomycin. In slices treated with sisomicin, HIP profiles evolved with a time course similar to untreated slices; however, the neurons in such treated slices nevertheless showed substantial recovery after hypoxia was terminated, as indicated below.

Figure 2:
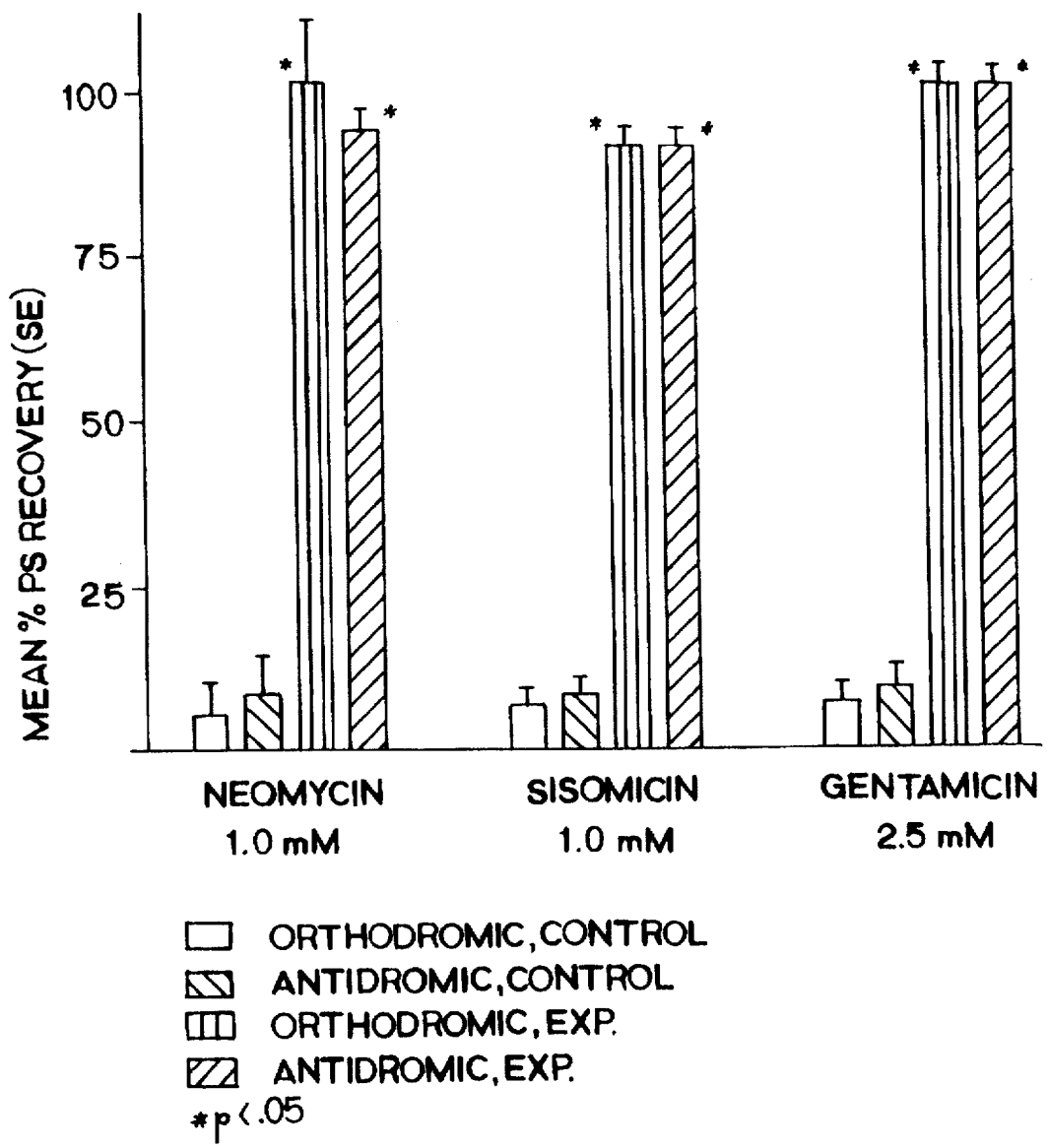
FIG. 2 depicts protection of neuronal activity in hippocampal tissue slices subjected to a period of oxygen deprivation (Example 3).
Figure 3:
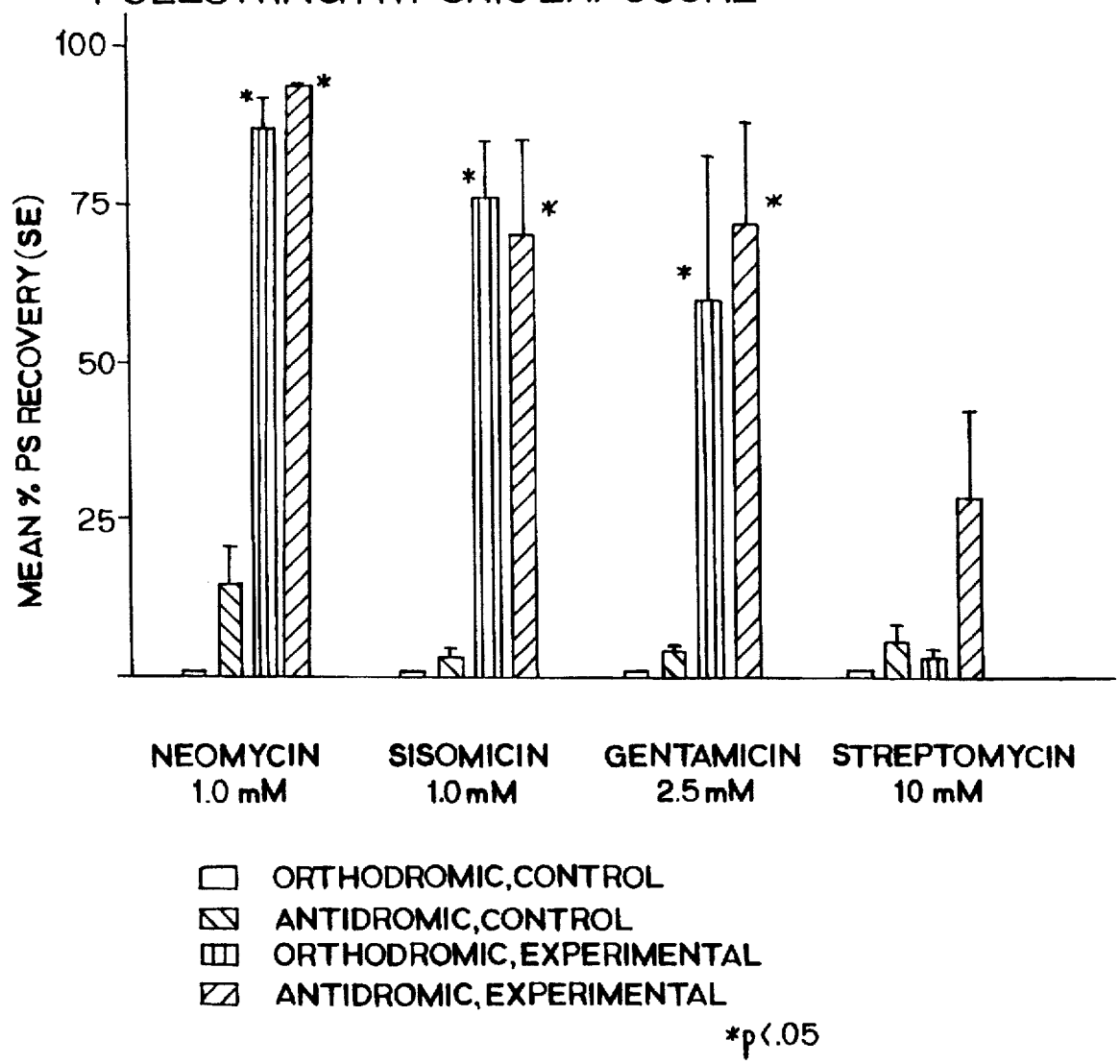
FIG. 3 depicts protection of neuronal activity in hippocampal tissue slices subjected to a period of oxygen deprivation; these tissue slices were periodically stimulated by electrodes throughout the hypoxic period, which provides a more rigorous test than "unstimulated" tissue slices (Example 3).
Figure 4:
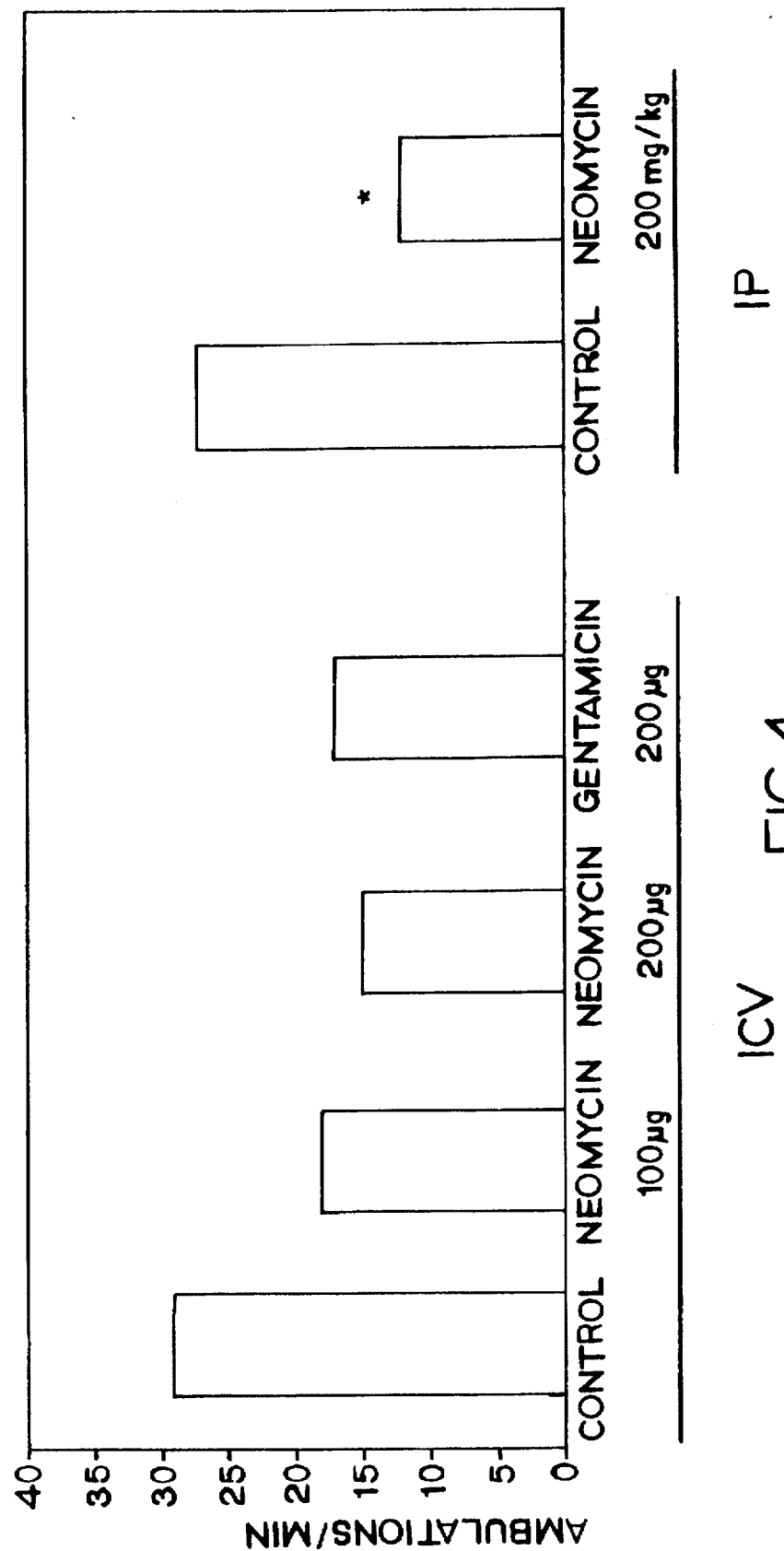
FIG. 4 depicts protection against surgically-induced ischemic brain damage in gerbils, as evidenced by suppression of hyperactivity, when injected into either the ventricles of the brain (ICV) or into the peritoneal (abdominal) cavity (IP) (Example 4).
Figure 5:
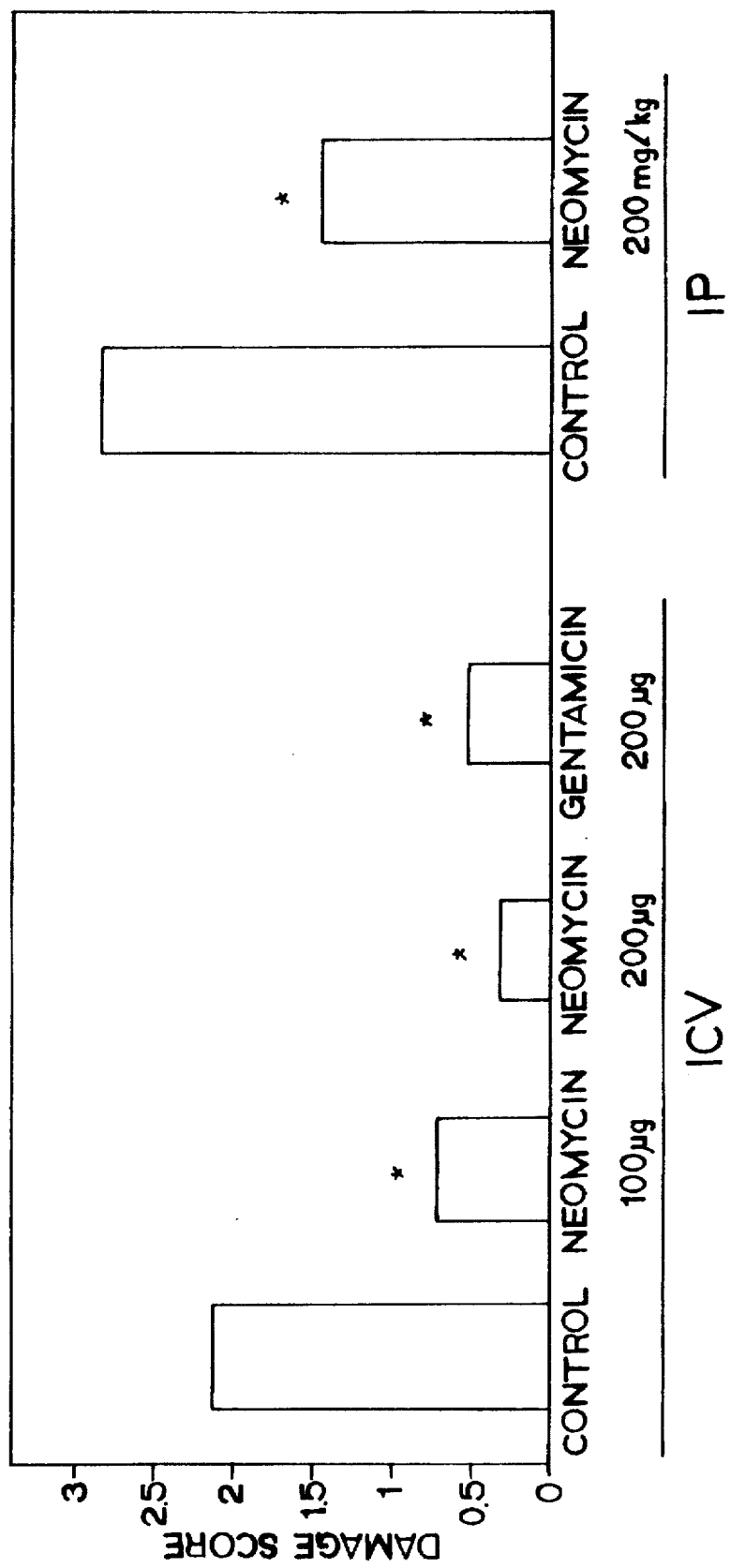
FIG. 5 depicts protection against surgically-induced ischemic brain damage in gerbils, as evidenced by suppression of histologically observed neuronal damage (Example 4).
Figure 6:
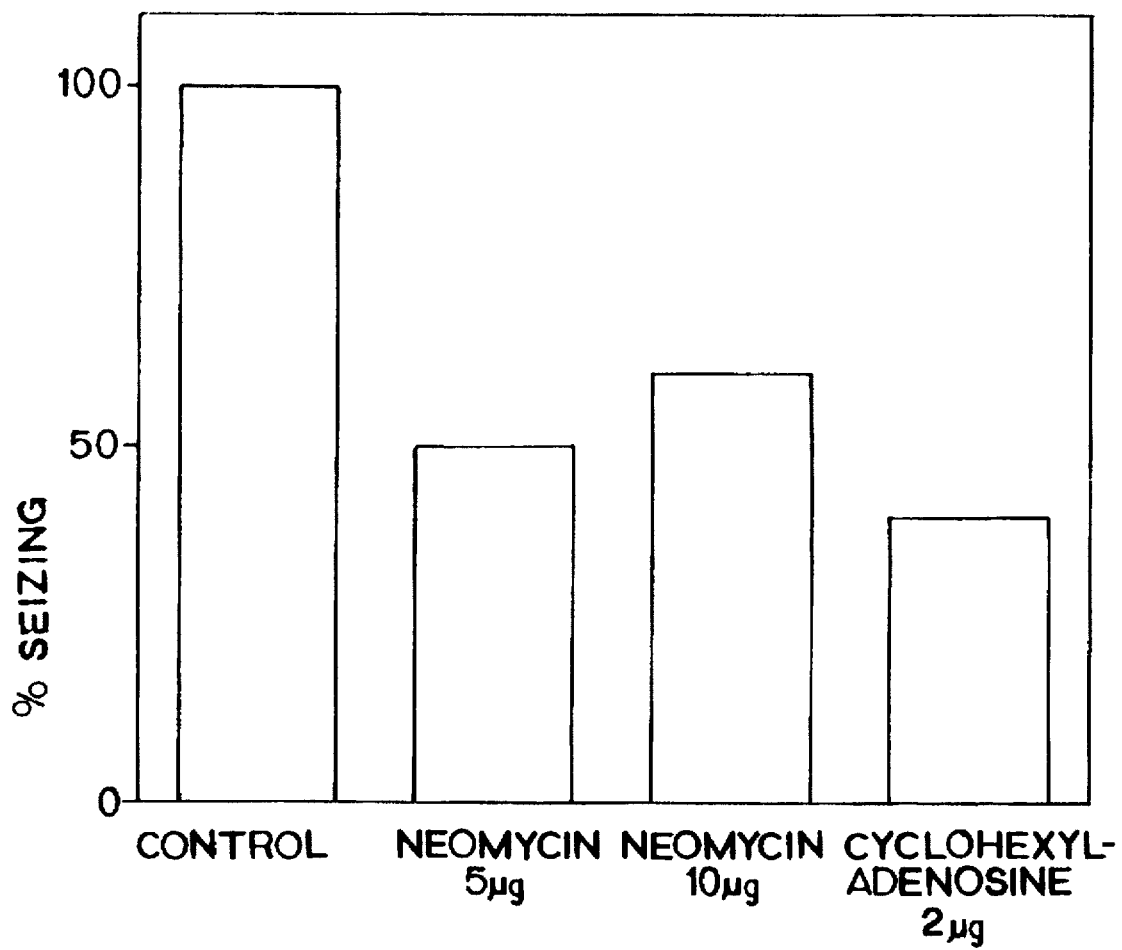
FIG. 6 depicts protection against seizure activity in rats induced by PTZ, a convulsant drug (Example 5).
Figure 7:
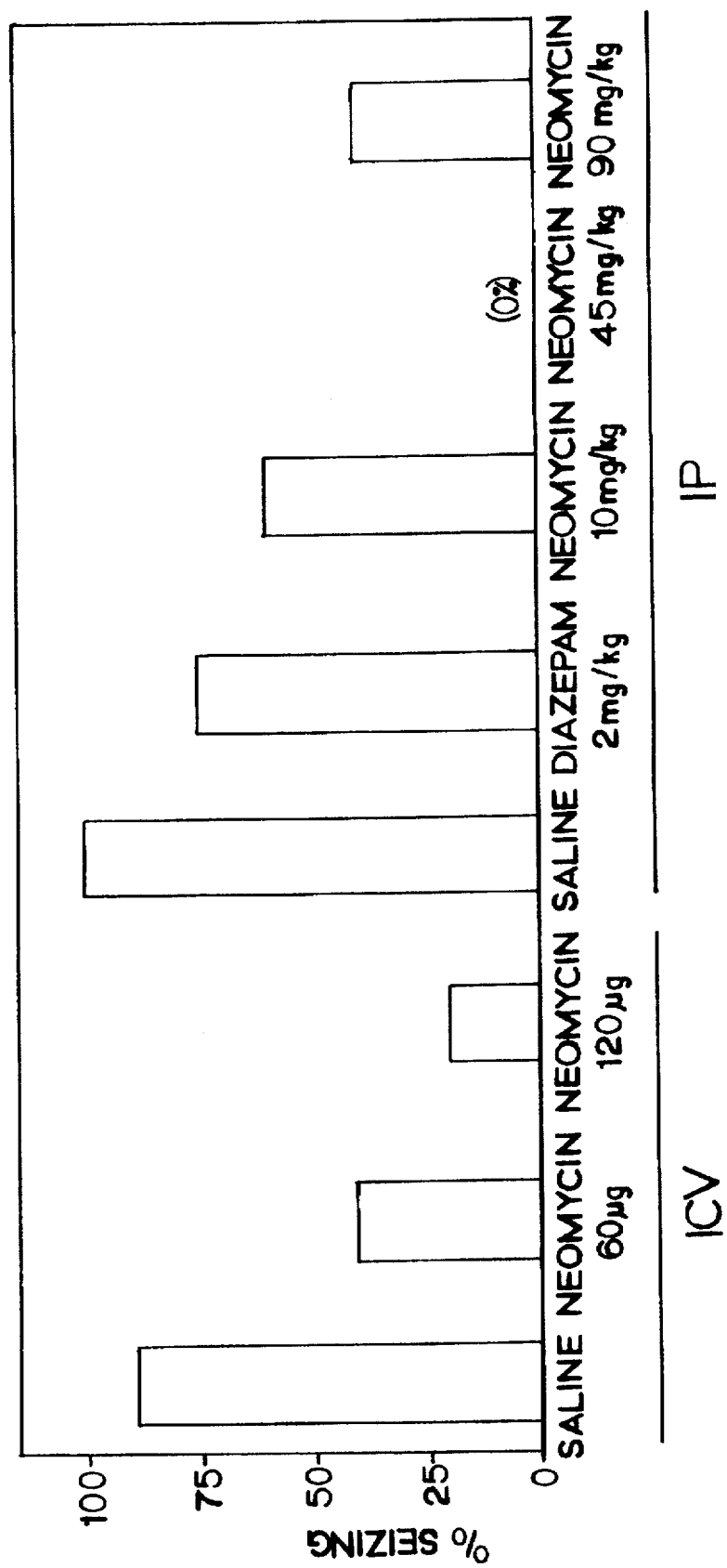
FIG. 7 depicts protection against seizure activity in rats induced by PTZ when injected into brain ventricles (ICV) or peritoneal cavity (IP) (Example 6).
Figure 8:
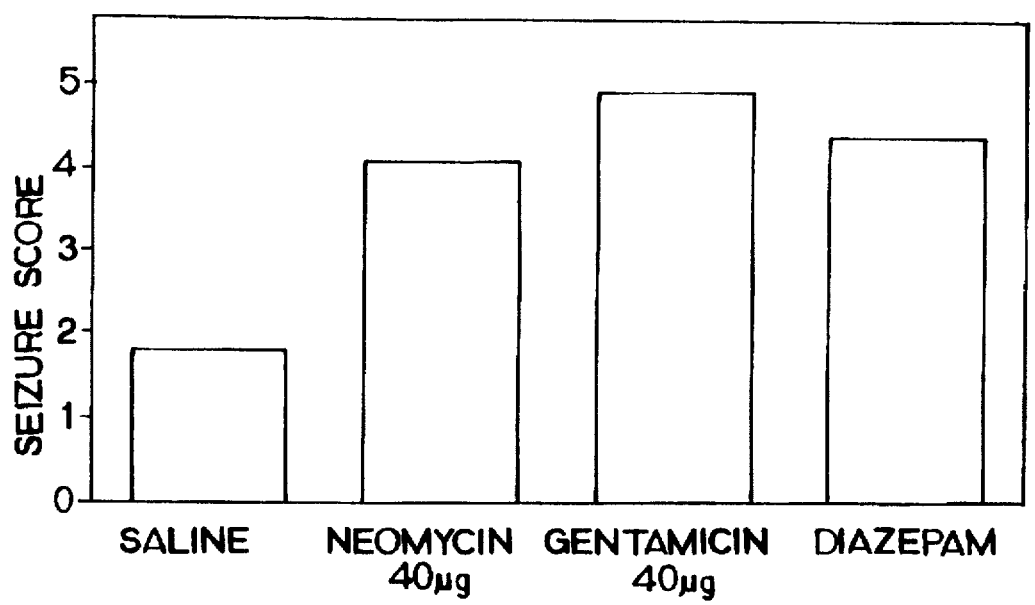
FIG. 8 depicts protection against seizure activity in rats induced by electroshock treatment (Example 7).

In summary, in these assays, three aminoglycosides (neomycin, gentamicin and sisomicin) which had been shown to be relatively potent in inhibiting N-channel activity provided a high level of neuronal protection against hypoxia, while a fourth aminoglycoside, streptomycin, provided a lower degree of neuroprotection. Furthermore, the level of neuroprotective efficacy was directly correlated with potency in inhibiting conotoxin binding at N-channels. These results confirm a direct correlation between the N-channel blockage and neuroprotective efficacy, and they provide direct evidence to support the teachings of the invention. Data from these tests is displayed in FIGS. 2 and 3.

EXAMPLE 4

REDUCTION OF ISCHEMIC DAMAGE, IN VIVO, IN GERBILS

An additional set of tests were done to determine whether aminoglycosides which block activity at N-type $Ca^{2+}$ channels would reduce actual ischemic damage, in vivo, in adult mammals. Mongolian gerbils were used; these are widely used in surgical models for testing anti-ischemia drugs, because most gerbils (about 60–70%) do not have an arterial structure called the Circle of Willis, which connects the anterior and posterior cerebral circulation in the brain. In gerbils that lack the Circle of Willis, a relatively simple surgical procedure involving a brief occlusion of the two common carotid arteries can generate complete forebrain ischemia comparable to cardiac arrest (this type of ischemia is usually referred to as global ischemia, and is distinct from focal ischemia, which is limited to only a portion of the brain, as normally occurs during a stroke). These carotid arteries in gerbils lie relatively close to the skin as they pass through the neck, and they can be reached and occluded for a brief span of time without inflicting severe surgical damage on the animals. However, since some gerbils have a Circle of Willis, a sufficiently large number of animals need to be treated to provide a statistical likelihood that the number of animals that do and do not have a Circle of Willis are comparable in both the test (treated) group and the control (untreated) group.

Prior to ischemia, the animals were pretreated with neomycin or gentamicin, which generally provided the most effective neuroprotective effects in the in vitro and in vivo tests described in Examples 1–2 and 5–7. Two routes of administration were used. The animals were injected just prior to the onset of ischemia via either intraperitoneal (IP) or intracerebral ventricular (ICV) injection. For ICV injections, the drug is delivered directly into the brain, thereby bypassing the blood brain barrier (BBB). For IP injections, the drug is injected into the peritoneal cavity of the abdomen where it is absorbed into the circulation and must cross the BBB to be utilized by the brain. Control animals received the saline drug vehicle by the same routes of administration. Temperature throughout the procedure was maintained at 34° C. Thirty minutes after drug or saline administration, the common carotid arteries were surgically clamped for 5 minutes, then released to allow restoration of blood flow to the brain.

Motor activity was used as one measure of neural damage, as described in Kuroiwa et al 1991. The animals were placed in an activity chamber that measured locomotor activity using an interruptible light beam. This test was done during the period 24 to 30 hours after the onset of ischemia. Results are reported in ambulations per minute. Animals with high levels of brain damage exhibit hyperactive motor activity more frequently; accordingly, high ambulation/min rates indicate higher levels of brain damage.

Four days after ischemia, the animals were sacrificed and perfused with paraformaldehyde, and the brains were removed and placed in 30% sucrose in phosphate buffered saline (PBS). After 2–3 days in sucrose-PBS, the brains were sectioned, the sections were stained, and the hippocampal region was analyzed for histological damage. Damage was scored on a scale from 0 to 3, with 0 indicating no visible damage and 3 indicating extensive damage. Scoring was done on a double blind basis using numerical codes to identify brain samples during scoring.

The resulting data indicated that injection of either neomycin or gentamicin into the lateral ventricle protected the brain against ischemic damage. At both of the concentrations tested (100 or 200 µg/animal), neomycin provided a statistically significant (at the 95% confidence level) reduction in histological damage, compared to control animals. Gentamicin, which in prior tests had been shown to be less potent than neomycin in reducing N-channel activity than neomycin, was tested at only 1 dosage (200 µg/animal); it also produced a statistically significant (95% level) reduction in histological damage compared to control animals.

As indicated by Table 3, ICV injection of neomycin and gentamicin also clearly caused a drop in post-ischemia locomotor hyperactivity averages, compared to controls; however, because of the limited numbers of animals tested and the fairly large standard deviations, this reduction in locomotor activity did not reach a 95% level of statistical significance. Reductions in histologic damage by neomycin (100 µg) or gentamicin were statistically significant at the 95% confidence level; neomycin (200 µg) protection against histologic damage was significant at the 99% level.

TABLE 3

REDUCTION OF ISCHEMIC
DAMAGE BY VENTRICULAR INJECTION

| Group | Ambulations/min | Hist. damage score | # tested |
|---|---|---|---|
| Control | 29 ± 5 | 2.1 ± 0.9 | 4 |
| Neomycin, 100 µg/inj | 18 ± 12 | 0.7 ± 0.8 | 7 |
| Neomycin, 200 µg/inj | 15 ± 9 | 0.3 ± 0.5 | 8 |
| Gentamicin 200 µg/inj | 17 ± 8 | 0.5 ± 0.9 | 7 |

Intraperitoneal administration of neomycin using the same protocols also provided substantial protection, as indicated by reductions in both motor activity and histological damage. The ambulation reduction was statistically significant at the 98% level; the reduction in histological damage was statistically significant at a level higher than 99%.

TABLE 4

REDUCTION OF ISCHEMIC
DAMAGE BY INTRAPERITONEAL INJECTION

| Group | Ambulations/min | Damage score | # tested |
|---|---|---|---|
| Control | 27 ± 9 | 2.8 ± 0.4 | 5 |
| Neomycin, 200 mg/kg | 12 ± 7 | 1.4 ± 1.2 | 7 |

Accordingly, these data show that under the conditions tested, neomycin and gentamicin were able to prevent or reduce neuronal damage caused by actual ischemia in adult mammals in in vivo tests. The intraperitoneal injection tests also confirmed that neomycin was able to cross the mammalian blood brain barrier.

EXAMPLE 5

REDUCTION OF SEIZURE ACTIVITY IN MICE USING INTRA-CEREBRO-VENTRICULAR (ICY) INJECTION

In addition to the in vivo gerbil experiments described in Example 4, aminoglycosides were tested in various ways to evaluate their ability to inhibit experimentally-induced seizures in mice. In one set of tests, male Swiss Webster white mice weighing 20–25 grams were used. The animals (10 per group) were pre-injected with 3 microliters (µL) of either a saline solution (control group), or saline solution containing varying dosages of neomycin sulfate.

The injection was performed via the ICY route, to insure access of the neomycin to neurons; when these experiments were initially performed, questions concerning the ability of neomycin to penetrate the BBB had not yet been addressed. These injections were performed as described in Haley and McCormick 1957.

Twenty minutes after the injections, the animals were administered a dose of 70 mg/kg of the convulsion-inducing drug pentylenetetrazol (PTZ), injected subcutaneously in saline solution. Control animals treated with ICV saline have full seizures within seven minutes following this dose of PTZ. However, as indicated by Table 5, animals treated with five or ten micrograms of neomycin sulfate were substantially protected against seizures. These results illustrate that the neomycin has anticonvulsant properties approaching the potency of cyclohexyladenosine (CHA), a known anticonvulsant drug.

TABLE 5

PTZ-INDUCED SEIZURES IN MICE

| Experimental Group | # Aminals | % having seizures | Behavioral Side-Effects |
|---|---|---|---|
| Saline Controls | 10 | 100% | – |
| 5 µg Neomycin Sulfate | 10 | 50% | – |
| 10 µg Neomycin Sulfate | 10 | 60% | – |
| 2 µg Cyclohexyladenosine | 10 | 40% | +++ |

A point of particular significance is that no behavioral side effects were observed in neomycin-treated animals; by contrast, CHA-treated animals displayed various behavioral side effects such as ataxia (lack of muscular control, as evidenced by an inability to walk properly) and sedation. Although not measured in these particular tests, CHA also is known to provoke hypotension and bradycardia (abnormally low heartbeat rate). The absence of such adverse side effects when aminoglycosides were used is regarded as a major advantage of aminoglycoside therapy in comparison with other anticonvulsants.

EXAMPLE 6

SEIZURE CONTROL IN RATS, USING ICV OR IP INJECTION

Seizure studies were also performed in male Sprague Dawley rats (250–300 grams). In these studies, cannulas were implanted in the lateral cerebral ventricles of several animals so that the test drugs could be administered directly into the lateral ventricle of the brain. The drugs being tested were administered 15 minutes before the administration of a convulsant drug, PTZ, at a dose of 60 mg/kg (in a saline vehicle) injected subcutaneously.

A second series of experiments was performed where neomycin sulfate was administered by the IP 30 minutes prior to PTZ injection. These are referred to as the IP studies in Table 6. The ability of the neomycin to inhibit seizures when administered via this route indicated that neomycin was able to permeate through the BBB and exert a therapeutic effect inside the brain even though it was injected into the abdomen.

TABLE 6

ICV OR IP PROTECTION AGAINST SEIZURES IN RATS

| Experimental Group | # Animals | % having seizures | Behavioral side-effects |
|---|---|---|---|
| ICV administration | | | |
| Saline | 9 | 89% | – |
| Neomycin (60 ug) | 5 | 40% | – |
| Neomycin (120 ug) | 5 | 20% | – |
| IP administration | | | |
| Saline | 8 | 100% | – |
| Diazepam (2 mg/kg) | 4 | 75% | ++ |
| Neomycin (10 mg/kg) | 5 | 60% | – |

TABLE 6-continued

ICV OR IP PROTECTION AGAINST SEIZURES IN RATS

| Experimental Group | # Animals | % having seizures | Behavioral side-effects |
|---|---|---|---|
| Neomycin (45 mg/kg) | 4 | 0% | – |
| Neomycin (90 mg/kg) | 5 | 40% | – |

These results show that neomycin has anticonvulsant effects in rats, even when administered into the abdomen in a manner that requires it to cross the BBB. In addition, these results confirm and support the mice results from the standpoint of showing an absence of undesired behavioral side effects.

EXAMPLE 7

REDUCTION OF ELECTROCONVULSIVE SEIZURES

The ability of aminoglycosides to reduce and control electroconvulsive seizures (ECS) has also been tested. This was accomplished using a set of platinum electrodes placed subcutaneously in two skull regions of Swiss Webster (20–25 gram) mice. The stimulus voltage was 22 mv at a duration of 0.125 mSec.

The seizures were graded on a severity scale of one to six. A score of six represented a complete absence of seizure activity, while a score of one represented the presence of a full tonic-clonic seizure with total hind leg extension. Test drugs were administered via the ICV route in a total volume of 2.5 microliters, 15 minutes prior to the administration of the electroconvulsive shock. The results of this experiment are illustrated in Table 7.

TABLE 7

EFFECTS OF NEOMYCIN ON ELECTROCONVULSIVE SEIZURES

| Experimental Group | # of Animals | Seizure Score | Behavioral Effects |
|---|---|---|---|
| Saline | 14 | 1.8 | – |
| 40 ug Neomycin | 13 | 4.1 | – |
| 40 ug Gentamicin | 8 | 4.9 | – |
| 5 ug Diazepam | 13 | 4.4 | + |

The results of these experiments show that both of the aminglycosides tested were able to inhibit electrically-induced seizures in a manner similar to that of diazepam, but with fewer behavioral effects.

Examples 5–7 demonstrate that using aminoglycosides to inhibit calcium flow into neurons via the N-channel can reduce convulsions using two entirely different seizure paradigms. These results attest to the ability of aminoglycosides to reduce and control undesirable and excessive neuronal activation in several different models which involve excess neurotransmitter release. The N-channel blocking capacity of the agents therefore has a functional correlate that makes them clinically useful for the treatment of neurological disease.

EXAMPLE 8

PLATELET AGGREGATION ASSAYS

Binding tests which involve neurons tend to be difficult, tedious, time-consuming, and expensive to carry out, for various reasons. Tests involving cell fragments require either neuronal cell culture, or the sacrifice of live animals.

However, neurons cannot be cultured easily in the laboratory; they require expensive nutrient media to sustain their growth, and they often require glial cells growing alongside them. In addition, neurons that reproduce adequately in laboratories are usually derived from cell lines that were cancerous in an animal or human, or that were genetically transformed in the lab using cancer-causing viruses or other transformation techniques, which raises questions about how accurately they serve as models of normal non-cancerous cells.

To minimize the requirement for neuronal testing in the preliminary stages of evaluating candidate aminoglycosides, the Applicant has developed an N-channel screening test which involves blood cells, which is much easier, faster, and more convenient to work with than neurons. This newly developed screening test uses blood platelets, which can be obtained in fresh supply in very large numbers, such as from humans who donate blood. The blood is treated using standard procedures to generate platelet-rich plasma. If the plasma is treated with 20 micromolar (μM) adenosine diphosphate (ADP), the ADP will under normal conditions induce platelet aggregation, a key step in the natural formation of blood clots inside the body.

The Applicant has discovered that (1) blood platelets contain N-channels on their surfaces; (2) platelet aggregation is mediated by N-channel activity; and, (3) ADP-induced platelet aggregation can be inhibited, in a quantitative manner, by agents which can block N-channel activity and which can block conotoxin binding to platelets.

By way of illustration, neomycin, gentamycin, and streptomycin were tested in two independent assays, for (1) inhibition of ADP-induced platelet aggregation, and (2) inhibition of omega conotoxin binding to platelets. The approximate results from the initial tests are shown in Table 8, wherein $IC_{50}$ is the inhibitory concentration which prevented platelet aggregation in 50 % of the cell samples tested.

TABLE 8

| AMINOGLYCOSIDE ACTIVITY INVOLVING BLOOD PLATELETS | | |
|---|---|---|
| Aminoglycoside | Aggregation inhibition ($IC_{50}$) | Conotoxin blockage |
| Neomycin | 500 μM | 1 μM |
| Gentamicin | 2000 μM | 5 μM |
| Streptomycin | 5000 μM | 15 μM |

These results indicate a direct quantitative relationship between the ability of various aminoglycosides to inhibit platelet aggregation and to inhibit conotoxin binding; furthermore, these results are completely consistent with the relative binding strengths reported in Knaus et al 1987, which involved conotoxin binding to neurons.

Accordingly, this discovery reveals a new, simple, and convenient screening assay involving blood platelets. Using this assay, any aminosaccharide which is a candidate for use as described herein can be tested quickly and easily for its ability to block activity at N-type calcium channels. Aminosaccharide compounds that show substantial activity in the platelet assay can be further evaluated to determine whether they protect neurons of the central or peripheral nervous system against excitotoxic damage, using additional screening tests such as the various in vitro and in vivo assays described in Examples 1-7.

Thus, there has been shown and described a new and useful method for using aminoglycosides that can penetrate the blood-brain barrier and suppress N-channel activity in neurons to reduce excitotoxic neuronal damage. Although this invention has been exemplified for purposes of illustration and description by reference to certain specific embodiments, it will be apparent to those skilled in the art that various modifications and alterations of the illustrated examples are possible. Any such changes which derive directly from the teachings herein, and which do not depart from the spirit and scope of the invention, are deemed to be covered by the claims that follow.

REFERENCES

Boast, C. A., "Neuroprotection after brain ischemia: Role of competitive NMDA antagonists," pp. 691–698 in Cavalheiro et al 1988

Buchan, A., and Pulsinelli, W. A., "Hypothermia but not the NMDA antagonist MK-801 attenuates neuronal damage in gerbils subjected to transient global ischemia," *J. Neurosci.* 10:311–316 (1990)

Caputy, A. J , et al, "The neuromuscular blocking effect of various antibiotics on normal rat skeletal muscle: A quantitative comparison," *J. Pharmacol. Exp. Ther.* 217:369–378 (1981)

Cavalheiro, E. A., et al, *Frontiers in Excitatory Amino Acid Research* (Alan R. Liss, NYC, 1988)

Fairchild, M. D , et al, "A hypoxic injury potential in the hippocampal slice, " *Brain Res* 453:357–361 (1988)) .

Ferry, D. R., et al, "Desmethoxyverapamil labelling . . . " *Naunyn Schmiederberg's Arch. Pharmacol.* 327:183–187 (1984)

Haley and McCormick, *British Journal of Pharmacology* 12:12 (1957)

Hossmann, K. A., "Post-ischemic resuscitation of the brain: selective vulnerability versus global resistance," *Progr. Brain Res.* 63:3–17 (1985)

Kasai, H., et al, "Presynaptic Ca-antagonist omega-conotoxin irreversibly blocks N-type Ca-channels in chick sensory neurons," *Neurosci. Res.* 4:228–235 (1987)

Knaus, H. G., et al, "Neurotoxic aminoglycoside antibiotics are potent inhibitors of 125-I Omega-Conotoxin GVIA binding to guinea pig cerebral cortex membranes," *Naunyn Schmiederberg's Arch. Pharmacol.* 336:583–586 (1987)

Krause, G. S., et al, "Brain cell death following ischemia and reperfusion: A proposed biochemical sequence," *Critical Care Medicine* 16:714–726 (1988)

Krieglstein, J., *Pharmacology of Cerebral Ischemia* (Wissenschaftliche Verlagsgesellschaft mbH, Stuttgart, 1989)

Krieglstein, J., and Oberpichler, H., *Pharmacology of Cerebral Ischemia* (Wissenschaftliche Verlagsgesellschaft mbH, Stuttgart, 1990)

Kuroiwa, T., et al, "Locomotor hyperactivity and hippocampal CA1 injury after transient forebrain ischemia in gerbils," *Neurosci. Lett.* 122:141–144 (1991)

Lanier, W. L., et al, "The effects of MK-801 . . . in primates," *J. Cerebr. Blood Flow and Metabol.* 10:252–261 (1990)

Meyer, F. B., et al. "Focal cerebral ischemia: Pathophysiolic mechanisms and rationale for future avenues of treatment," *Mayo Clin. Proc.* 62:35–55 (1987)

Michenfelder, J. D., et al. "Evaluation of MK-801 in a canine model," *Brain Research* 481:228–234 (1989)

Miller, R. J., "Multiple calcium channels and neuronal function," *science* 235:46–52 (1987)

Nowycky, M. C., et al, "Three types of neuronal calcium channels with different calcium agonist sensitivity," *Nature* 316:440–443 (1985)

Olney, J. W., et al, "Pathological changes induced in cerebrocortical neurons by phencyclidine and related drugs," *Science* 244:1360–1362 (1989)

Olney, J. W., et al, "NMDA antagonist neurotoxicity: Mechanism and prevention," *Science* 254:1515–1518 (1991)

Pittinger, C. and Adamson, R., "Antibiotic blockade of neuromuscular function," *Ann. Rev. Pharmacol.* 1972:169–184 (1972)

Sande, M. A., and Mandell, G. L., "Antimicrobial agents: The aminoglycosides," in Gilman and Goodman, eds., The *Pharmacological Basis of Therapeutics* (Macmillan Publ., NY, 1985)

Sheardown, M. J., et al, "NBQX: a neuroprotectant for cerebral ischemia," *Science* 247:571–574 (1990)

Tarnawa, I., et al, "GYKI 52466, an inhibitor of spinal reflexes, is a potent quisqualate antagonist," pp. 538–546 in Labee and Rosenthal, eds., *Amino Acids: chemistry, Biology and Medicine* (1990)

Wallis, R. A., et al, "Protective effects of felbamate against hypoxia in the rat hippocampal slice," *Stroke* 23:457–551 (1992)

Wauquier, A., et al, "Cerebral resuscitation: Pathophysiology and Therapy," *Neurosci. Behav. Rev.* 11:287–306 (1987)

Whisnant, J. P., et al Classification of cerebrovascular diseases," *Stroke* 21(4): 637–676 (1990)

Wright, J. M., and Collier, B., "The effects of neomycin upon transmitter release and action," *J. Pharmacol. Exp. Ther.* 200: 567–587 (1977)

I claim:

1. A method of reducing excitotoxic neuron damage in mammals suffering such damage, by means of injecting into a mammalian bloodstream a therapeutically effective quantity of a selected aminoglycoside which reduces neuronal calcium ion uptake through N-type calcium ion channels on neuronal surfaces, wherein the selected aminoglycoside has;

(a) at least one saccharide ring having at least five atoms:

(b) more than two primary amine groups; and, (c) a potency stronger than streptomycin in reducing calcium ion uptake into neurons through N-type calcium ion channels, and wherein the selected aminoglycoside can penetrate mammalian blood-brain barriers and reduce excitotoxic damage to neurons in an adult mammalian brain in a therapeutically effective manner if injected into a mammal suffering such excitotoxic neuron damage and wherein said aminoglycoside is selected from the group consisting of aminoglycoside antibiotics and their pharmaceutically acceptable salts and isomers.

2. The method of claim 1 wherein the aminoglycoside is selected from the group consisting of neomycin, gentamicin, sisomycin, and pharmaceutically acceptable salts and isomers thereof.

3. The method of claim 1 wherein the aminoglycoside is administered by venous injection.

4. The method of claim 1 wherein the aminoglycoside is administered by continuous intravenous infusion.

5. The method of claim 1 wherein the aminoglycoside is injected into a mammalian bloodstream by means of a slow-release device emplaced in the body of a patient.

6. The method of claim 1 wherein the aminoglycoside is administered to a patient during a surgical procedure that disrupts normal blood circulation in the patient.

7. A method of suppressing seizures in mammals by means of administering to a mammal suffering from seizure activity, a therapeutically effective quantity of a selected aminoglycoside which is known to reduce neuronal calcium ion uptake through N-type calcium ion channels on neuronal surfaces, wherein the selected aminoglycoside has;

a) at least one saccharide ring having at least five carbon atoms;

(b) more than two primary amine groups; and, (c) a potency stronger than streptomycin in reducing calcium ion uptake into neurons through N-type calcium ion channels, and wherein the selected aminoglycoside can penetrate mammalian blood-brain barriers and suppress glutamate release by neurons in an adult mammalian brain if injected into a mammalian bloodstream and wherein said aminoglycoside is selected from the group consisting of aminoglycoside antibiotics and their pharmaceutically acceptable salts and isomer.

8. The method of claim 7 wherein the aminoglycoside is an aminoglycoside selected from the group consisting of neomycin, gentamicin, sisomycin, and pharmaceutically acceptable salts and isomers thereof.

9. The method of claim 7 wherein the aminoglycoside is administered to the mammal by means of a slow-release device emplaced in the body of a patient.

10. The method of claim 7 wherein the aminoglycoside is administered by venous injection.

11. The method of claim 7 wherein the aminoglycoside is administered by continuous intravenous infusion.

12. The method of claim 7 wherein oral administration of an aminoglycoside is enhanced to increase absorption into circulating blood after oral administration.

13. A method of suppressing glutamate release by neurons in a mammal suffering from a neurodegenerative disease which involves excitotoxic overstimulation of neurons as a component of the neurodegenerative disease, by means of administering to the mammal a therapeutically effective quantity of a selected aminoglycoside which is known to reduce neuronal calcium ion uptake through N-type calcium ion channels on neuronal surfaces, wherein the selected aminoglycoside has:

(a) at least one saccharide ring having at least five carbon atoms;

(b) more than two primary amine groups; and, (c) a potency stronger than streptomycin in reducing calcium ion uptake into neurons through N-type calcium ion channels, and wherein the selected aminoglycoside can penetrate mammalian blood-brain barriers and suppress glutamate release by neurons in an adult mammalian brain if injected into a mammalian bloodstream and wherein said aminoglycoside is selected from the group consisting of aminoglycoside antibiotics and their pharmaceutically acceptable salts and isomer.

14. The method of claim 13 wherein the aminoglycoside is an aminoglycoside selected from the group consisting of neomycin, gentamicin, sisomycin, and pharmaceutically acceptable salts and isomers thereof.

15. The method of claim 13 wherein the aminoglycoside is administered to the mammal by means of a slow-release device emplaced in the body of a patient.

* * * * *